United States Patent
Doyle et al.

(10) Patent No.: US 10,617,551 B2
(45) Date of Patent: Apr. 14, 2020

(54) ARM SUPPORT SYSTEMS

(71) Applicant: LEVITATE TECHNOLOGIES, INC., San Diego, CA (US)

(72) Inventors: Mark C. Doyle, Del Mar, CA (US); Helen A. Doyle, Del Mar, CA (US)

(73) Assignee: ENHANCE TECHNOLOGIES, LLC, San Diego, CA (US)

(*) Notice: Subject to any disclaimer, the term of this patent is extended or adjusted under 35 U.S.C. 154(b) by 0 days.

(21) Appl. No.: 15/494,966

(22) Filed: Apr. 24, 2017

(65) Prior Publication Data

US 2017/0224517 A1   Aug. 10, 2017

Related U.S. Application Data

(63) Continuation of application No. PCT/US2015/057263, filed on Oct. 24, 2015.

(60) Provisional application No. 62/068,547, filed on Oct. 24, 2014.

(51) Int. Cl.
| | |
|---|---|
| *A61F 2/68* | (2006.01) |
| *A61F 5/01* | (2006.01) |
| *B25J 9/00* | (2006.01) |
| *B25J 19/00* | (2006.01) |
| *A61H 1/02* | (2006.01) |

(52) U.S. Cl.
CPC ............. *A61F 5/013* (2013.01); *B25J 9/0006* (2013.01); *B25J 19/0016* (2013.01); *A61F 2005/0134* (2013.01); *A61F 2005/0179* (2013.01); *A61H 1/0274* (2013.01)

(58) Field of Classification Search
CPC ........ A61F 2/68; A61F 5/013; A61F 5/05858; A61F 2005/0134; A61F 2005/0179; A61F 2005/0141; A61F 2005/0144; A61F 2005/0146; A61F 2005/0148; A61F 2005/0151; A61F 2005/0153; A61H 1/0274
USPC .......................................................... 248/98
See application file for complete search history.

(56) References Cited

U.S. PATENT DOCUMENTS

| | | | | |
|---|---|---|---|---|
| 2,310,566 | A * | 2/1943 | Anderson | ........... A61F 5/05808 602/19 |
| 2,535,489 | A * | 12/1950 | Edwards | .................... A61F 2/58 623/24 |
| 4,180,870 | A * | 1/1980 | Radulovic | ............... A61F 5/013 601/33 |
| 4,669,451 | A * | 6/1987 | Blauth | .................... A61F 5/013 482/901 |

(Continued)

*Primary Examiner* — Nkeisha Smith
(74) *Attorney, Agent, or Firm* — Vista IP Law Group LLP; William A. English

(57) ABSTRACT

Systems and methods are provided for supporting an arm of a user using a harness configured to be worn on a body of a user; and an arm support coupled to the harness configured to support an arm of the user, the arm support configured to accommodate movement of the arm while following the movement without substantially interfering with the movement of the user's arm. One or more compensation elements may be coupled to the arm support to apply an offset force to at least partially offset a gravitational force acting on the arm as the user moves and the arm support follows the movement of the user's arm, the one or more compensation elements providing a force profile that varies the offset force based on an orientation of the arm support.

14 Claims, 28 Drawing Sheets

(56) References Cited

U.S. PATENT DOCUMENTS

| | | | |
|---|---|---|---|
| 6,113,562 A * | 9/2000 | Bonutti | A61F 5/013 602/16 |
| 8,591,441 B2 * | 11/2013 | Bonutti | A61F 5/013 602/16 |
| 9,205,017 B2 * | 12/2015 | Doyle | A61H 1/0281 |
| 9,345,606 B2 * | 5/2016 | Bonutti | A61F 5/013 |
| 9,572,702 B2 * | 2/2017 | Bonutti | A61F 5/013 |
| 9,737,374 B2 * | 8/2017 | Doyle | A61B 90/60 |
| 9,999,534 B2 * | 6/2018 | Doyle | A61F 5/0118 |
| 2017/0100295 A1 * | 4/2017 | Bonutti | A61F 5/013 |
| 2017/0189257 A1 * | 7/2017 | Lan | A63B 21/00178 |
| 2017/0203432 A1 * | 7/2017 | Andrianesis | A61F 2/54 |
| 2017/0224516 A1 * | 8/2017 | Bonutti | A61F 5/05858 |
| 2018/0028274 A1 * | 2/2018 | Doyle | A61B 90/60 |

\* cited by examiner

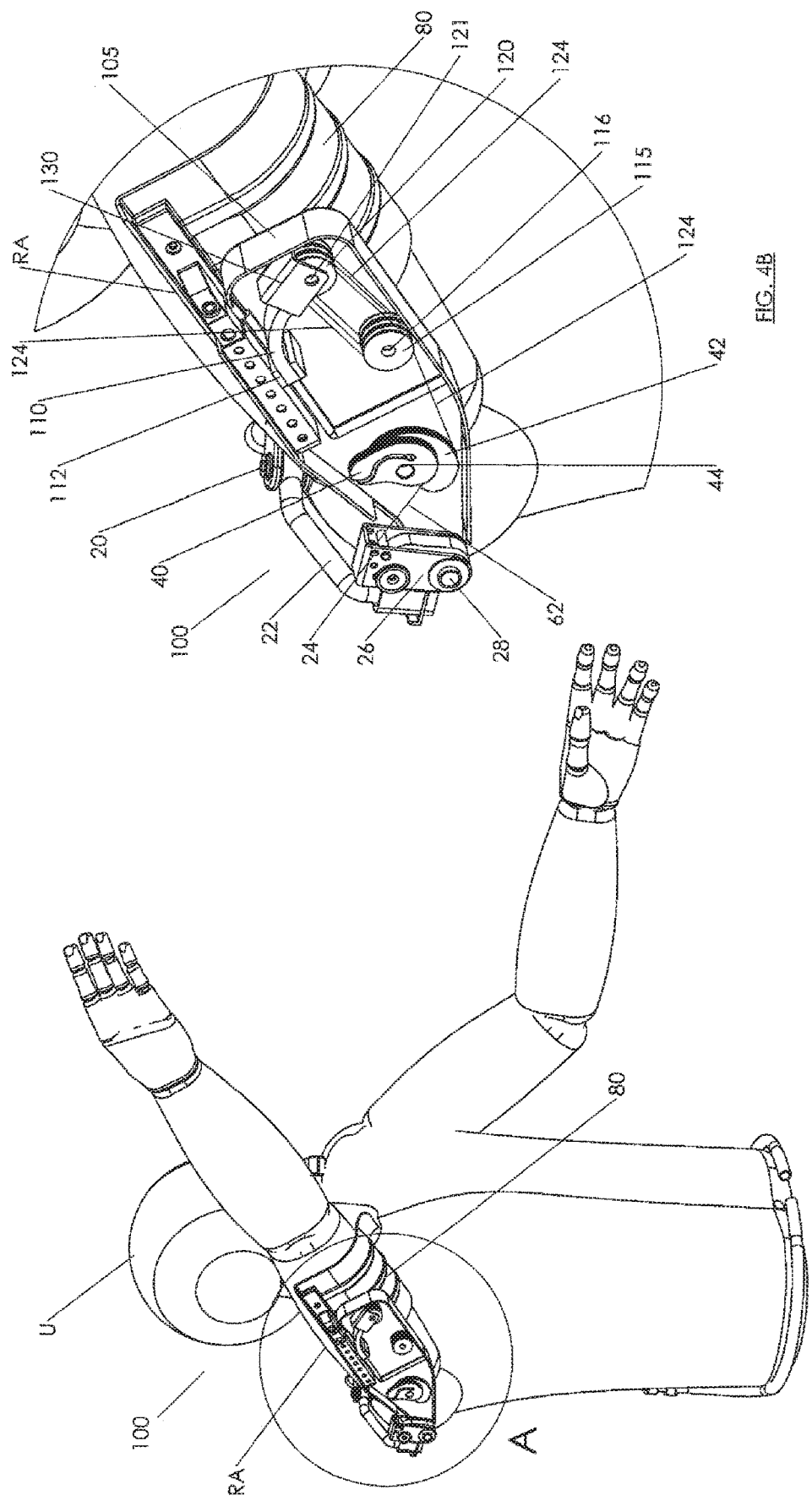

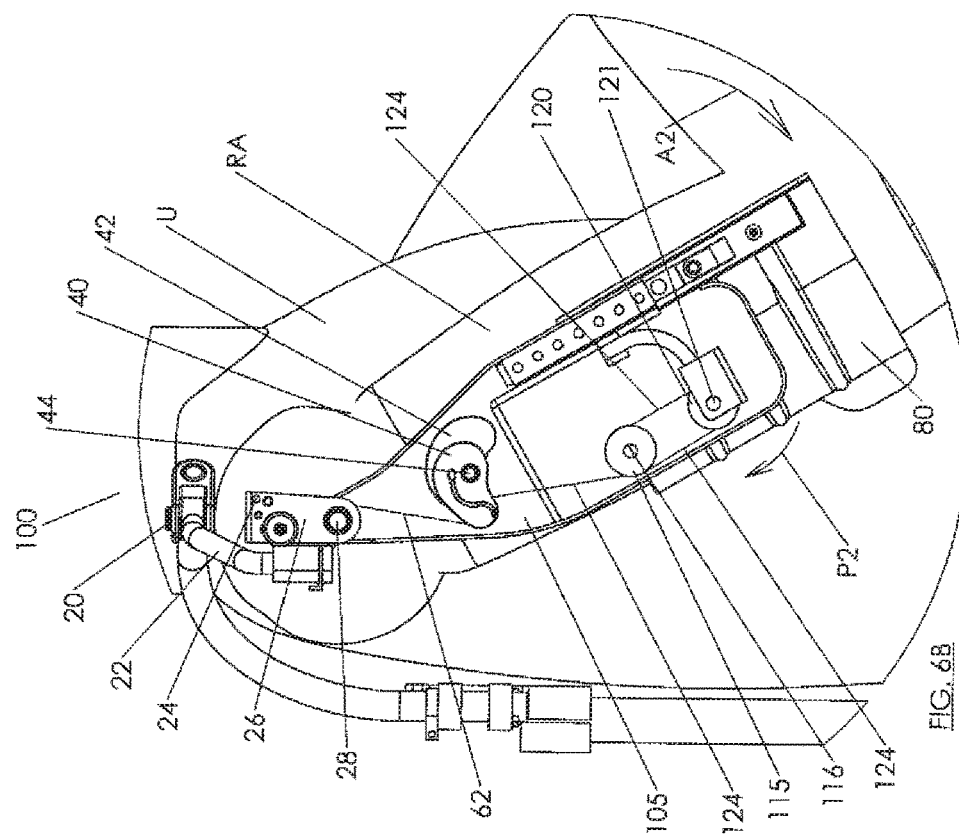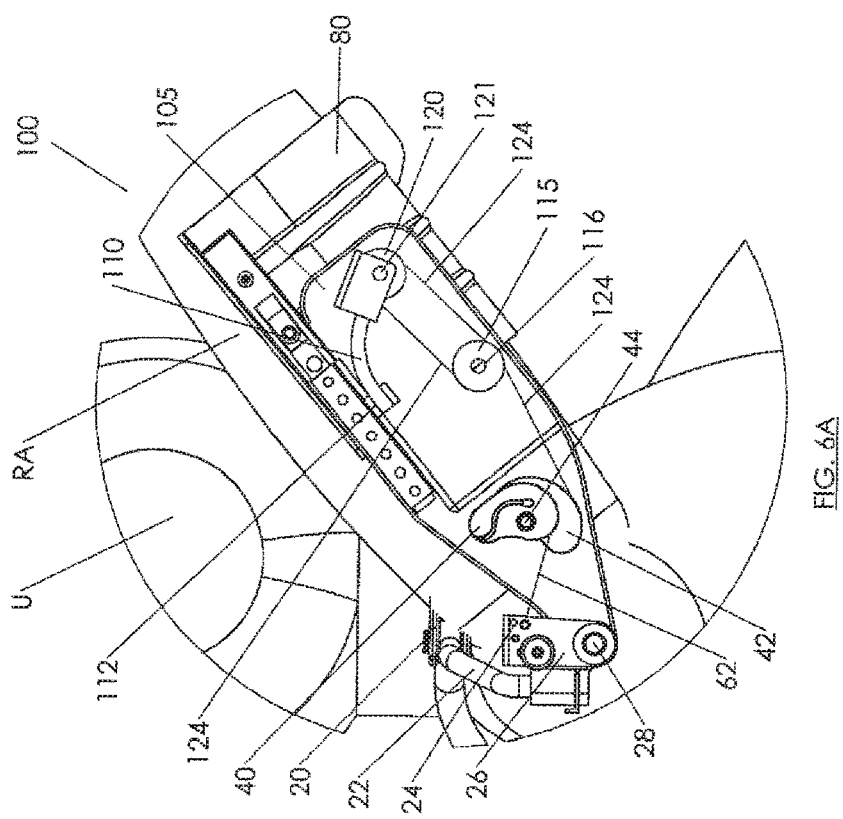

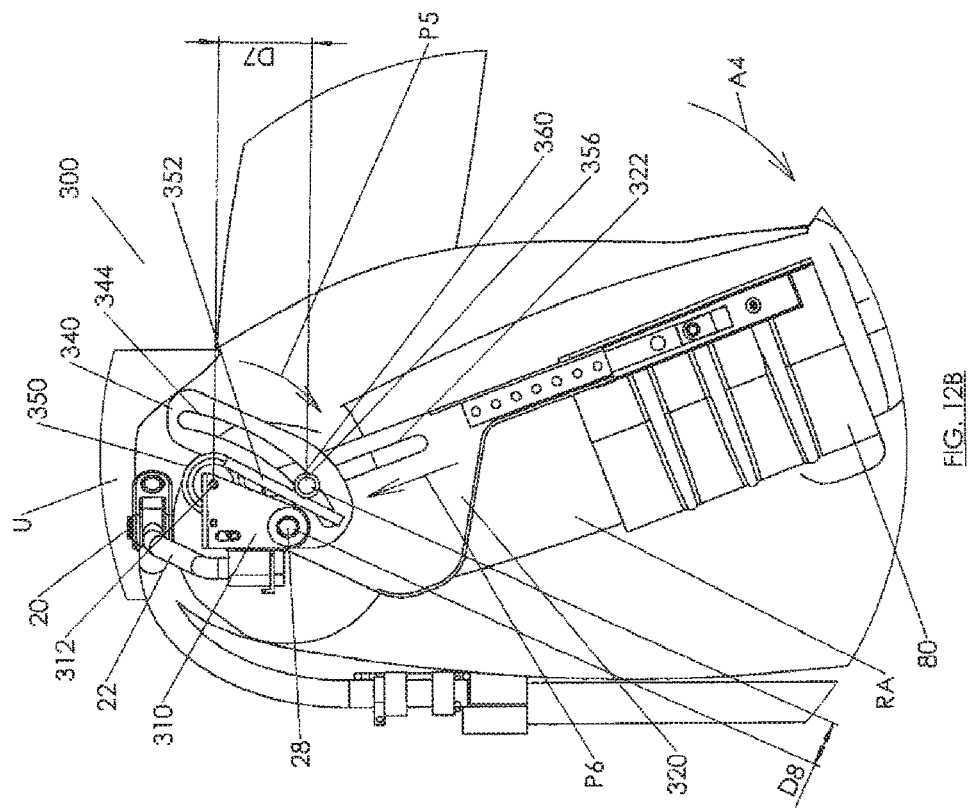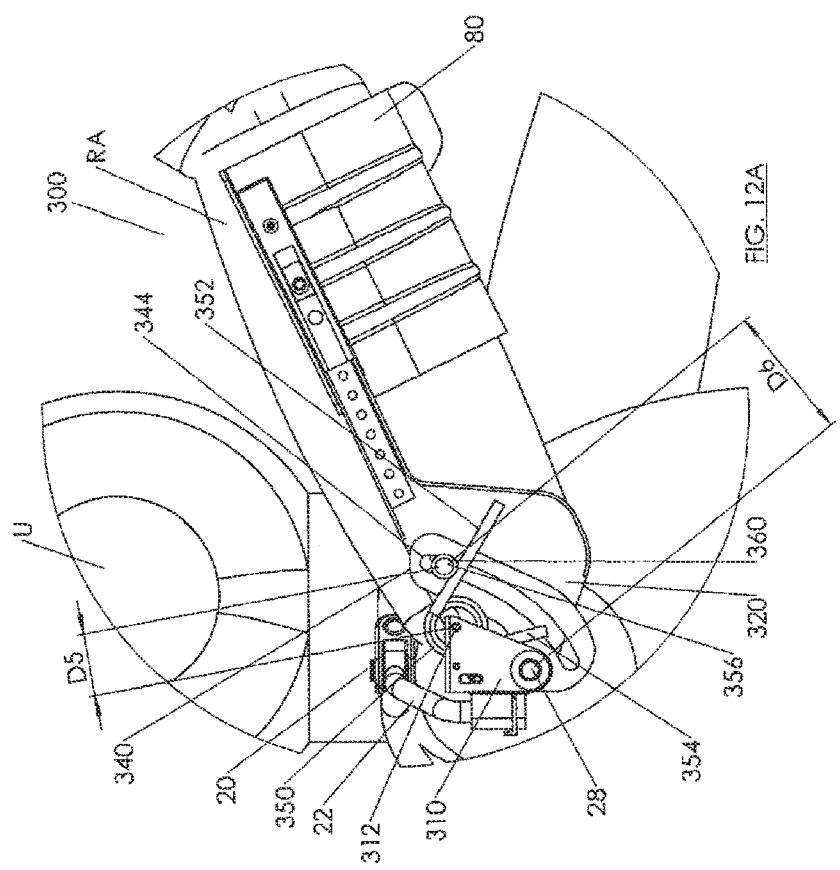

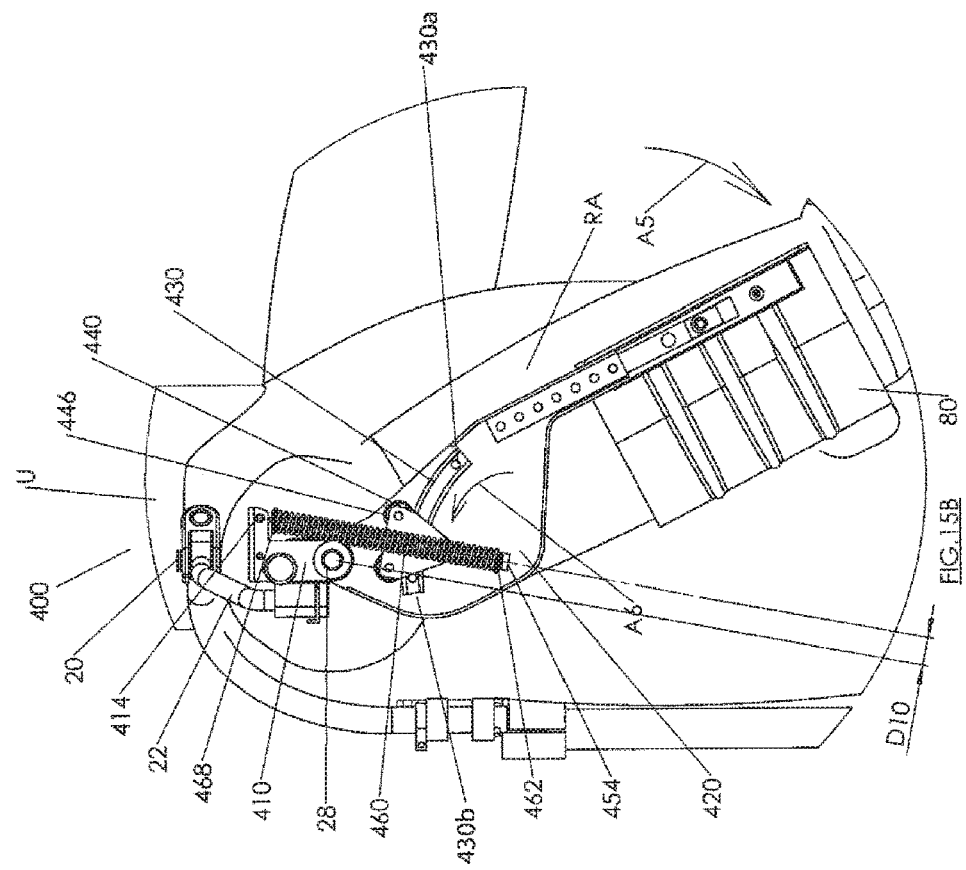
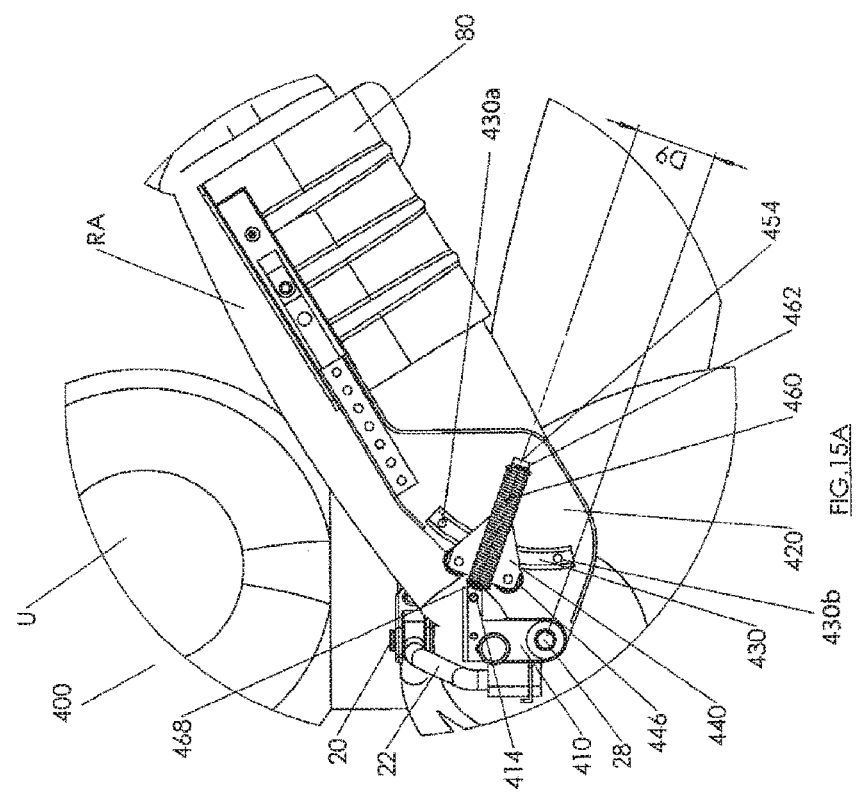

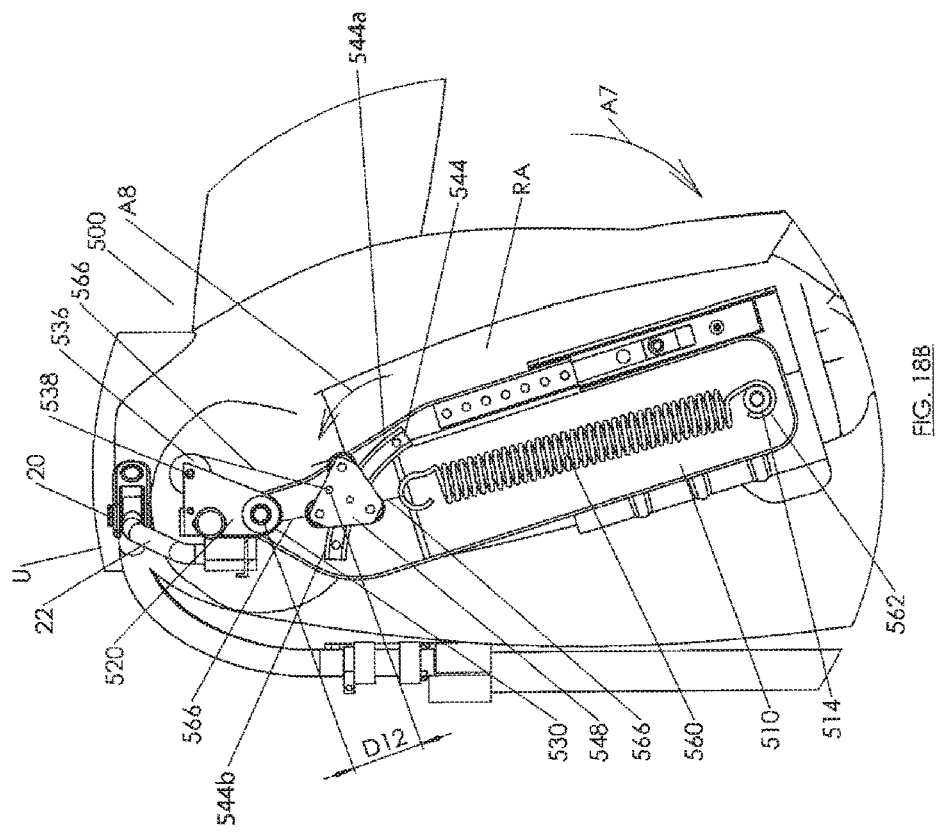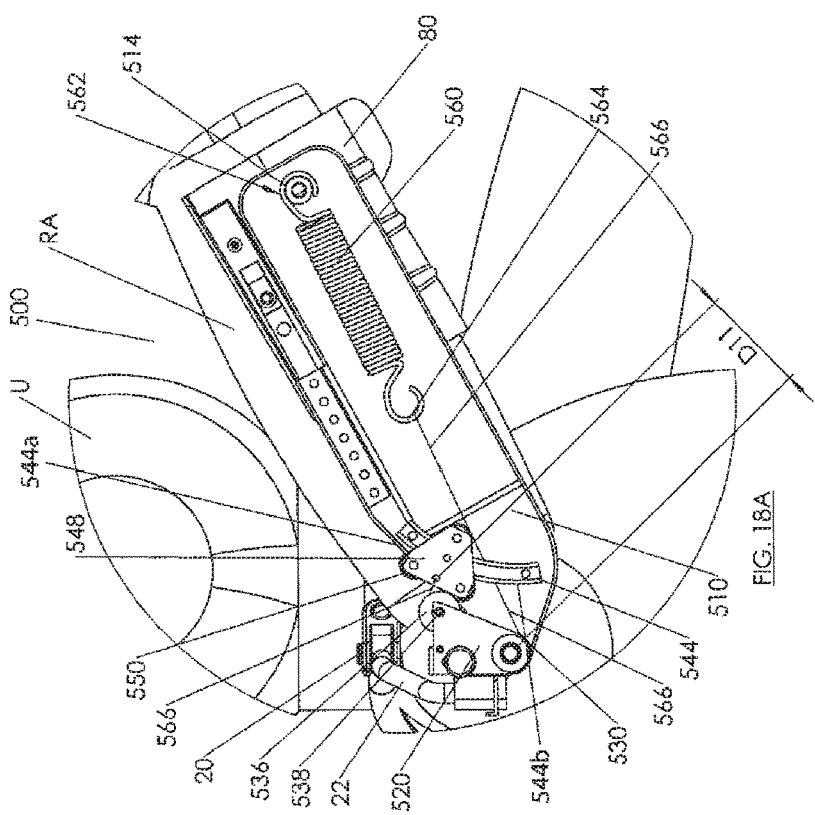

ARM SUPPORT SYSTEMS

RELATED APPLICATION DATA

The present application is a continuation of co-pending international application Serial No. PCT/US2015/057263, filed Oct. 24, 2015, which claims benefit of provisional application Ser. No. 62/068,547, filed Oct. 24, 2014, the entire disclosures of which are expressly incorporated by reference herein. In addition, the present application is related to application Ser. No. 13/353,268, filed Jan. 18, 2012, Ser. No. 13/563,728, filed Jul. 31, 2012, and Ser. No. 14/102,466, filed Dec. 10, 2013, and provisional application Ser. Nos. 61/969,440, filed Mar. 24, 2014, and 61/977,060, filed Apr. 8, 2014, the entire disclosures of which are also expressly incorporated by reference herein.

FIELD OF THE INVENTION

The present invention relates to systems, devices, and methods for supporting a user's arms, for example, to adaptive arm support systems that support one or both of a user's arms, while allowing substantially free motion, e.g., to allow the user to perform one or more tasks for extended periods of time with one or both arms extended.

BACKGROUND

Numerous tasks require people to work with their arms outstretched, e.g., while operating hand tools or other equipment that they must at least partially support themselves. Examples include construction, surgery, dentistry, painting, dishwashing, and product assembly. Persons engaged in such activities may experience fatigue from prolonged muscular efforts required to resist the force of gravity on their arms in order to keep them extended. Weak or disabled persons may experience fatigue performing daily tasks. Static arm rests on chairs and work tables are only effective if the task is performed within a relatively restricted area, for example, at a computer keyboard. Tasks that involve a greater range of motion are not aided by static armrests.

Thus, there is a need for systems that may relieve fatigue experienced by persons performing tasks involving moderate to large ranges of motion and/or operating tools or other equipment.

SUMMARY

The present invention is directed to systems, devices, and methods for supporting a user's arms, for example, to adaptive arm support systems or devices that support one or both of a user's arms, while allowing substantially free motion, e.g., to allow the user to perform one or more tasks for extended periods of time with one or both arms extended.

An arm support system can be used to provide a lift force to a user's arm to aid in the performance of tasks requiring the extension and raising of the arms.

A spring-loaded arm support system is simple and does not require external power, but can have the unwanted side effect that spring force increases with displacement, making the spring force greatest at the lowest position of the arm (where lift is needed least).

Modification of the lift force on a user's arm is desirable, for example, by increasing the force when the arm is raised, and reducing the force when the arm is lowered.

A solution is provided by "disadvantaging" the spring as it deflects (and thus applies more net lift force), for example, by reducing its mechanical advantage on the system as the user's arm is lowered and the spring is deflected (increasing the force in the spring).

Some mechanisms for "disadvantaging" a spring may include:

a) Varying the angle of the tension element acting on the system, b) Varying radii in pulleys about which a tension element is wrapped, c) Combining the two above mechanisms, d) Moving the point of action and varying the angle of the tension element acting on the system, e) Moving the point of action and varying the leverage on a torsional spring mechanism, and/or f) Moving the point of action of a tension element on a system.

In accordance with one embodiment, a system is provided for supporting an arm of a user that includes a harness configured to be worn on a body of a user; an arm support coupled to the harness configured to support an arm of the user, the arm support configured to accommodate movement of the arm while following the movement without substantially interfering with the movement of the user's arm; and one or more compensation elements coupled to the arm support to apply an offset force to at least partially offset a gravitational force acting on the arm as the user moves and the arm support follows the movement of the user's arm, the one or more compensation elements providing a force profile that varies the offset force based on an orientation of the arm support.

In accordance with another embodiment, a method is provided for supporting an arm of a user during one or more tasks that includes placing a harness on the user, the harness comprising an arm support movable relative to the harness and including an arm rest; supporting a portion of the user's arm using the arm support such that the arm support subsequently follows movement of the user's arm; and performing one or more tasks involving movement of the user's arm, the arm support comprising one or more compensation elements that apply an offset force to at least partially offset a gravitational force acting on the arm as the user moves without substantially interfering in the movement, the one or more compensation elements providing a force profile that varies the offset force based on an orientation of the arm support.

In accordance with still another embodiment, a system is provided for supporting an arm of a user that includes a harness configured to be worn on a body of a user; an arm support comprising a first arm support segment pivotally coupled to the harness about a first vertical axis such that the first arm support segment is rotatable substantially horizontally about the first vertical axis relative to the harness, and a second arm support segment pivotally coupled to the first arm support segment at a hub such that the second arm support segment is rotatable about a second axis generally orthogonal to the first vertical axis; and one or more compensation elements carried by a chassis of the second arm support segment to apply an offset force to at least partially offset a gravitational force acting on the arm as the user moves and the arm support follows the movement of the user's arm. In an exemplary embodiment, the one or more compensation elements include a leaf spring including a first fixed end mounted to the chassis and a second free end; one or more chassis pulleys rotatably mounted to the chassis adjacent the second free end of the leaf spring; first and second coupled pulleys rotatably mounted to the chassis such that the first and second coupled pulleys rotate together; a first tension element wrapped at least partially around the one or more chassis pulleys and including a first end coupled to the second free end of the leaf spring and a second end coupled to the first coupled pulley; and a second tension element including a first end coupled to the second coupled pulley and a second end coupled to the hub.

In one embodiment, the one or more chassis pulleys may include a plurality of chassis pulleys, and the first tension element may be wrapped at least partially around each of the plurality of chassis pulleys to amplify a tension force applied by the leaf spring when the second free end is deflected to the first tension element. Optionally, at least one of the first and second coupled pulleys may have a noncircular profile such that the amplified tension force from the first tension element is modified based on an angular position of the second arm support segment about the second axis, thereby applying a variable offset force on the hub. In addition or alternatively, the one or more compensation elements may further include a plurality of spring pulleys rotatably mounted to the second free end of the leaf spring, and the first tension element may be wrapped at least partially around and between the spring pulleys and the chassis pulleys to provide a block and tackle apparatus.

In accordance with yet another embodiment, a system is provided for supporting an arm of a user that includes a harness configured to be worn on a body of a user; an arm support comprising a first arm support segment pivotally coupled to the harness about a first vertical axis such that the first arm support segment is rotatable substantially horizontally about the first vertical axis relative to the harness, and a second arm support segment pivotally coupled to the first arm support segment at a hub such that the second arm support segment is rotatable about a second axis generally orthogonal to the first vertical axis; and one or more compensation elements to apply an offset force to at least partially offset a gravitational force acting on the arm as the user moves and the arm support follows the movement of the user's arm. The one or more compensation elements may include a cam plate fixedly coupled to the hub and including a curvilinear track; a moving axle slidably mounted within a chassis slot in the chassis, the moving axle slidably disposed within the track of the cam plate such that the moving axle moves along the track and within the chassis slot as the second arm support segment is raised and lowered; and a spring including a first fixed end and a second end coupled to the moving axle such that the offset force increases as the moving axle moves along the track away from the second axis and decreases as the moving axle moves along the track towards the second axis.

In one embodiment, the spring may be an extension spring with the first fixed end mounted to the chassis, the one or more compensation elements may further include a pulley rotatably mounted to the moving axle; and a tension element wrapped at least partially around the pulley and including a first end coupled to the second end of the spring and a second end coupled to the hub such that, as the second arm support segment is lowered, the pulley moves towards the second axis as the moving axle moves along the track towards the second axis to reduce the offset force applied by the tension element, and, as the second arm support segment is raised, the pulley moves away from the second axis as the moving axle moves along the track away from the second axis to increase the offset force applied by the tension element.

In another embodiment, the spring may be a torsion spring with the first fixed end mounted to the hub, and the second end of the spring may be coupled to the moving axle such that, as the moving axle moves along the track towards the second axis the offset force is reduced, and, as the moving axle moves away from the second axis, the offset force is increased.

In accordance with still another embodiment, a system is provided for supporting an arm of a user that includes a harness configured to be worn on a body of a user; an arm support comprising a first arm support segment pivotally coupled to the harness about a first vertical axis such that the first arm support segment is rotatable substantially horizontally about the first vertical axis relative to the harness, and a second arm support segment pivotally coupled to the first arm support segment at a hub such that the second arm support segment is rotatable about a second axis generally orthogonal to the first vertical axis; and one or more compensation elements to apply an offset force to at least partially offset a gravitational force acting on the arm as the user moves and the arm support follows the movement of the user's arm. The one or more compensation elements may include a curvilinear track mounted to the second arm support segment; a carriage carried on the track such that the moving axle moves along the track and within the chassis slot as the second arm support segment is raised and lowered; and a spring including a first end coupled to the hub and a second end coupled to the carriage such that the offset force changes as the carriage moves along the track.

In accordance with yet another embodiment, a system is provided for supporting an arm of a user that includes a harness configured to be worn on a body of a user; an arm support comprising a first arm support segment pivotally coupled to the harness about a first vertical axis such that the first arm support segment is rotatable substantially horizontally about the first vertical axis relative to the harness, and a second arm support segment pivotally coupled to the first arm support segment at a hub such that the second arm support segment is rotatable about a second axis generally orthogonal to the first vertical axis; and one or more compensation elements to apply an offset force to at least partially offset a gravitational force acting on the arm as the user moves and the arm support follows the movement of the user's arm. The one or more compensation elements may include a first pulley rotatably mounted to the hub at the second axis; a second pulley rotatably mounted to the hub offset from the second axis; a curvilinear track mounted to the second arm support segment; a carriage carried on the track such that the moving axle moves along the track and within the chassis slot as the second arm support segment is raised and lowered; a spring including a first fixed end coupled to the second arm support segment and a second movable end; a tension element coupled between the second movable end of the spring and the carriage, the tension element wrapped at least partially around the first and second pulleys such that the offset force changes as the carriage moves along the track.

Other aspects and features of the present invention will become apparent from consideration of the following description taken in conjunction with the accompanying drawings.

BRIEF DESCRIPTION OF THE DRAWINGS

The present invention is best understood from the following detailed description when read in conjunction with the accompanying drawings. It will be appreciated that the exemplary devices shown in the drawings are not necessarily drawn to scale, with emphasis instead being placed on illustrating the various aspects and features of the illustrated embodiments.

FIGS. 4A and 5A are perspective views of another exemplary embodiment of an arm support system worn by a user to support the user's right arm, showing the user's arm raised and lowered, respectively.

FIGS. 4B and 5B are perspective details of the arm support system shown FIGS. 4A and 5A, respectively.

FIGS. 6A and 6B are side view details of the arm support shown in FIGS. 4A and 5A, respectively.

FIGS. 12A and 12B are side view details of the arm support shown in FIGS. 10A and 11A, respectively.

FIGS. 15A and 15B are side view details of the arm support shown in FIGS. 13A and 14A, respectively.

FIGS. 18A and 18B are side view details of the arm support shown in FIGS. 16A and 17A, respectively.

DESCRIPTION OF THE EXEMPLARY EMBODIMENTS

Figure 1A:
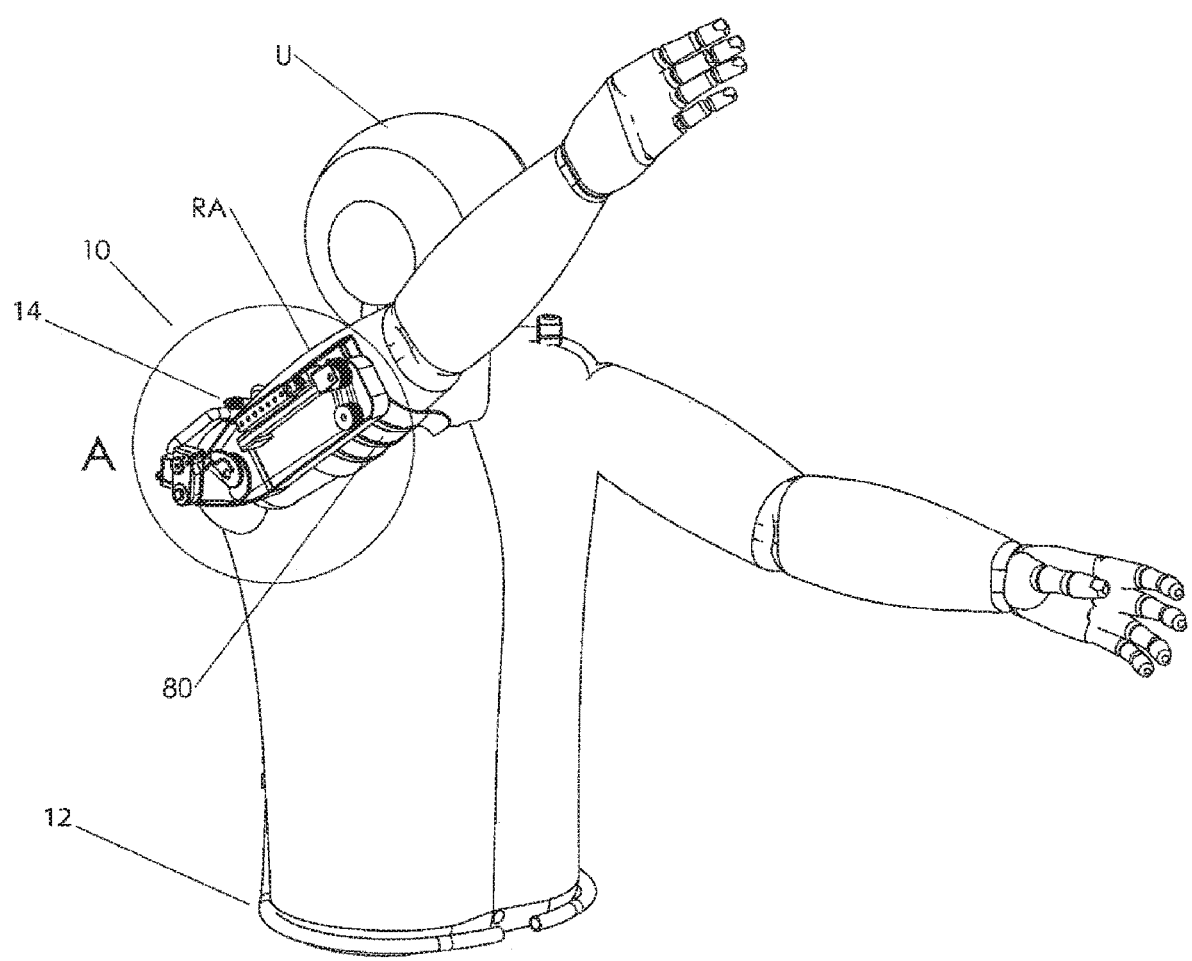
FIGS. 1A and 2A are perspective views of an exemplary embodiment of an arm support system worn by a user to support the user's right arm, showing the user's arm raised and lowered, respectively.

Turning to the drawings, FIGS. 1A-3B show a first exemplary embodiment of an adaptive arm support system 10 worn by a user U. Generally, the system 10 (similar to the other systems herein) includes a harness 12 and an arm support mechanism 14 for supporting one or both of the user's arms (only one arm support 14 shown supporting the user's right arm RA for simplicity). The harness 12 may include one or more of an attachment band configured to be worn around the user's torso, e.g., chest, waist, and/or hips, a shoulder harness configured to be worn over and/or around the user's shoulders, and/or one or more vertical supports, e.g., extending between the attachment band and the shoulder harness (all not shown for clarity), e.g., similar to the support systems disclosed in U.S. Publication Nos. 2012/0184880, 2014/0033391, and 2014/0158839, and in International Publication No. WO 2015/2015/157473, the entire disclosures of which are expressly incorporated by reference herein. In addition, the harness 12 may include a shoulder bracket and/or frame with a fixed end disposed above or adjacent to the user's shoulder to which other components of the system 10 may be coupled, e.g., to provide the arm support 14, which pivots about one or more axes relative to the shoulder bracket, similar to the systems in these publications. The systems herein may also include additional components similar to those disclosed in these publications, such as armrest 80, as desired.

Figure 2A:
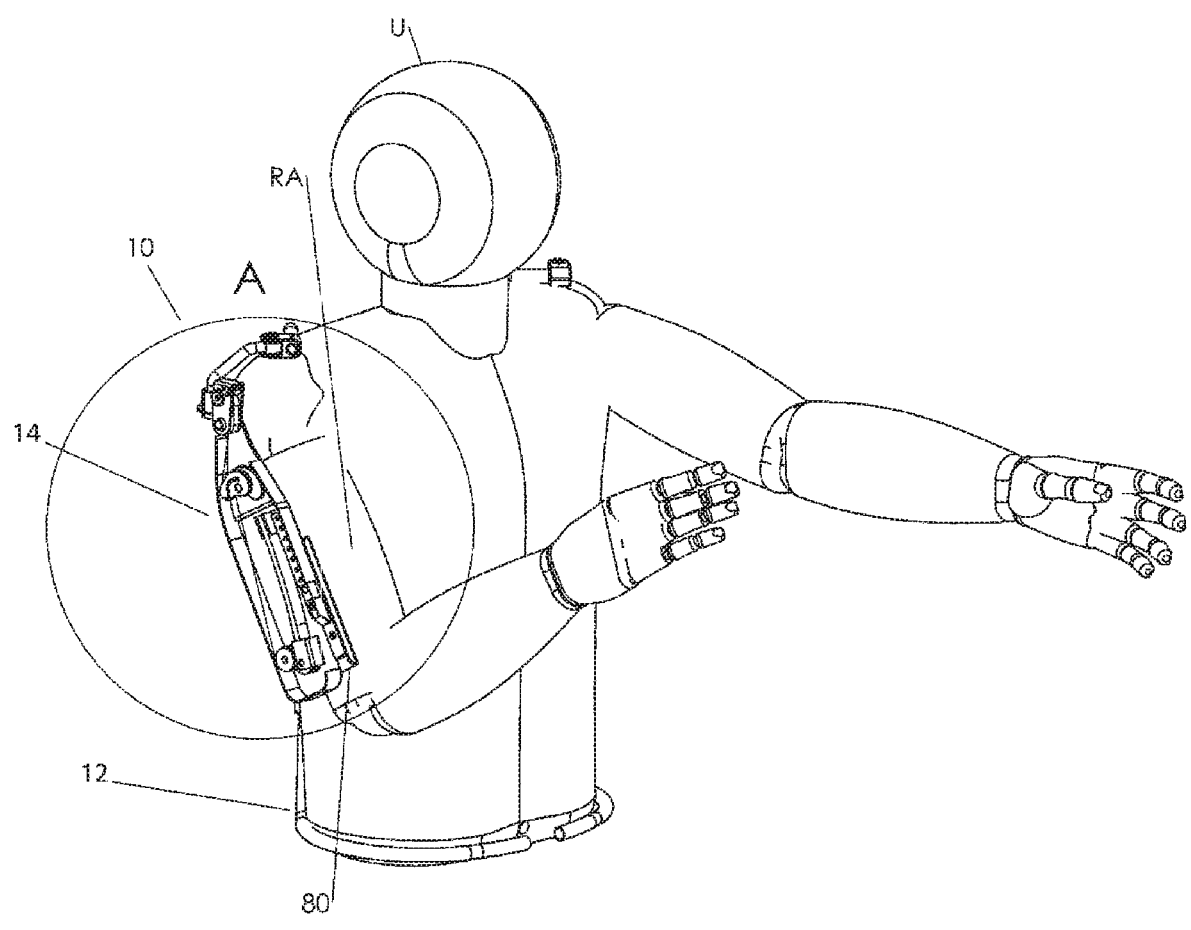

FIGS. 1A and 2A show perspective views of the adaptive arm support system 10, acting to provide a lift force on the user U's right arm RA through armrest 80. The arm support system 10 and the right arm RA are shown raised in FIG. 1A and lowered in FIG. 2A. Generally, the arm support mechanism 14 includes a first support segment, member, or shoulder bar 22 pivotally coupled to the harness 12, e.g., to the fixed shoulder bracket (not shown) on the harness 12, such that the shoulder bar 22 rotates horizontally about a vertical pivot 20, and a second support segment, member, bar, or chassis 30 pivotally coupled to the shoulder bar 22 such that the chassis 30 rotates vertically about a horizontal pivot 28.

The shoulder vertical pivot 20 may permit rotation of the arm support 14 about a substantially vertical axis. For example, the shoulder bar 22 connects shoulder vertical pivot 20 to a hub 26, which is fixedly mounted to the shoulder bar 22 and includes shoulder horizontal pivot 28, enabling rotation of the chassis 30 about a substantially horizontal axis. The chassis 30 provides a mounting structure for several components, e.g., contained within a housing or cartridge (not shown to facilitate identification of the internal components). For example, the chassis 30 may include one or more compensation elements, e.g., springs, pulleys, cables, and the like, that apply an offset force to at least partially offset a gravitational force acting on the arm RA as the user moves, e.g., providing a variable offset force based on the orientation of the arm RA.

For example, as shown in FIGS. 1B, 2B, 3A, and 3B, the chassis 30 may include a first pulley 40 and a second pulley 42 mounted thereto, which are joined together and move as one, e.g., rotating about axle 44. A first tension element, e.g., first cable, 62, is attached to the first pulley 40 and to anchor point 24 on the hub 26. A first end of leaf spring 70 is attached to the chassis 30 at cantilever fitting 74. The second, free end of the leaf spring 70 is attached to a pulley hub 72, which includes moving axle 54 about which zero, one, or more moving pulleys 50 rotate. Pulleys 50 may include tension element track or groove 52 (best seen in FIG. 1B). One or more stationary pulleys 56 may rotate about stationary axle 58, and may include a tension element track or groove 53. Together moving pulley(s) 50 and stationary pulley(s) 56 form a "block and tackle" mechanism by which force in a second tension element, e.g., second cable 66, may be amplified by multiplying the number of wraps of the second tension element 66 within the "block and tackle," and thus effectively increasing the number of tension elements working to deflect the leaf spring 70. The first end of second tension element 66 is attached to second pulley 42, and wraps about one or more of the moving pulley(s) 50 and stationary pulley(s) 56 (within tension element grooves 52 and 53 respectively). The second end of the second tension element 66 may be attached at one of various points, e.g., to the stationary axle 58 or to the moving axle 54. The number of wraps will determine the mechanical advantage of the "block and tackle." For example, if there are three stationary pulleys 56, and two moving pulleys 50, and the second tension element 66 is attached at the moving axle 54, then there will be five effective wraps of the second tension element 66 within the "block and tackle," providing a mechanical advantage of five. If (for example) the tension in the second tension element 66 is, at a given point, fifteen kilograms (15 Kg), the total force acting to deflect leaf spring 70 will be seventy five kilograms (15×5=75 Kg).

Figure 2B:
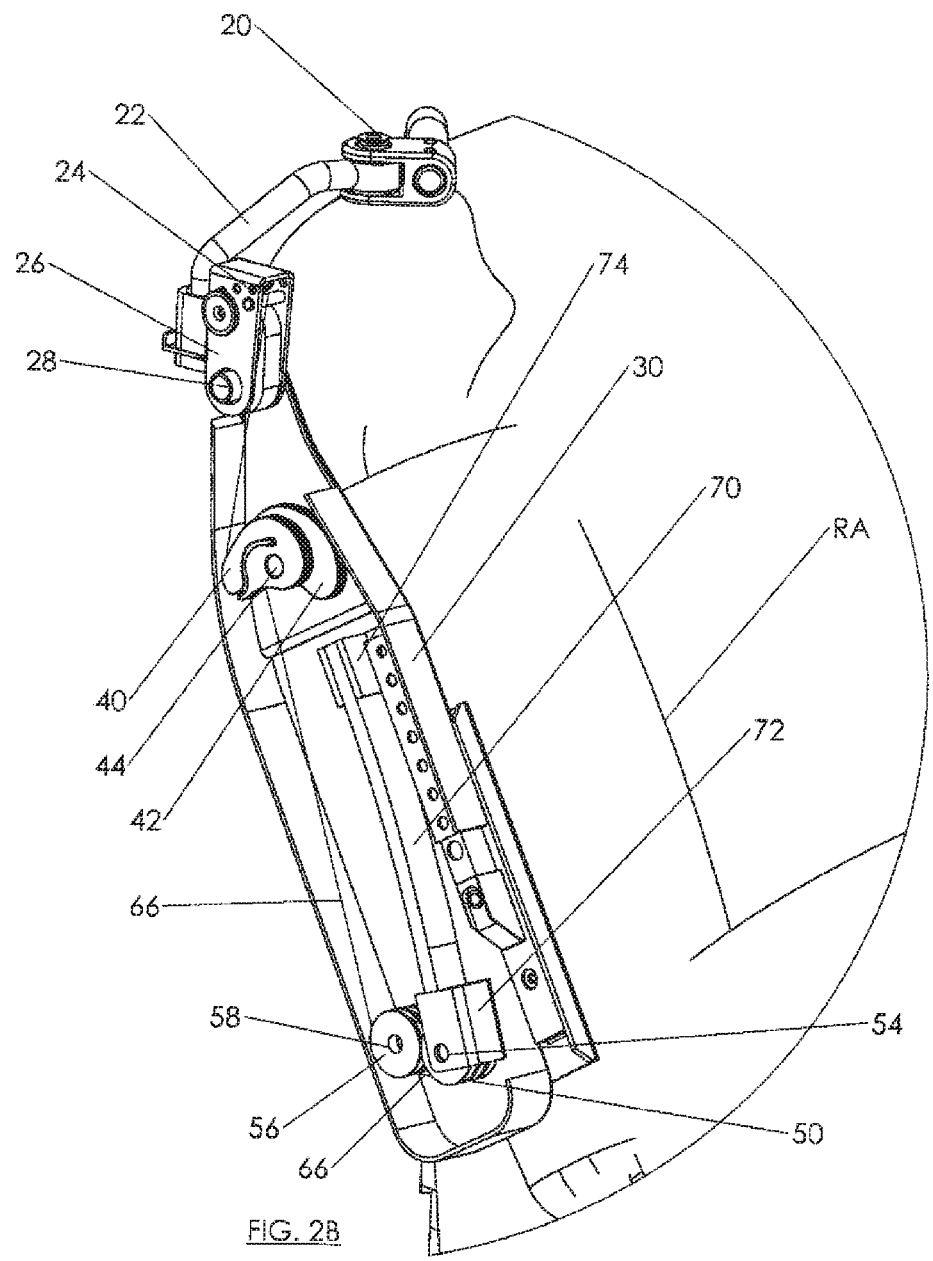
Figure 3B:
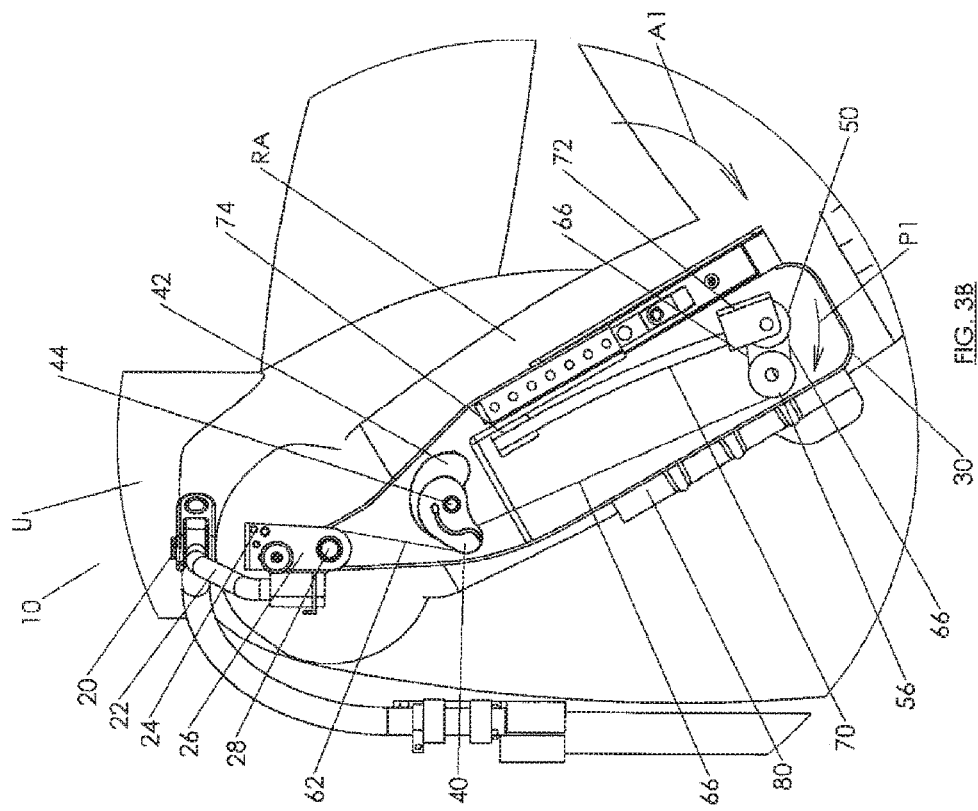
FIGS. 3A and 3B are side view details of the arm support shown in FIGS. 1A and 2A, respectively.

FIGS. 2B and 3B are details showing the arm RA and arm support 14 being lowered, as shown in FIG. 2A. In response to the user U lowering right arm RA, the first tension element 62 unwraps from the first pulley 40, and both the first pulley 40 and the second pulley 42 have, in response, rotated (together) about the axle 44. As the second pulley 42 rotates about the axle 44, the second tension element 66 is wrapped farther onto the second pulley 42. This, in turn, tightens the wraps of the second tension element 66 within the "block and tackle," drawing the moving pulley(s) 50 closer to the stationary pulley(s) 56, and deflecting the leaf spring 70 in response. The distance that the moving pulley(s) 50 draw closer to the stationary pulley(s) 56 are a function of the mechanical advantage provided by the number of effective wraps of the second tension element 66. For example, if there are five (5) effective wraps of the second tension element 66 within the "block and tackle," the moving pulley(s) 50 will draw closer to the stationary pulley(s) 56 approximately one fifth (⅕) of the change in length of the second tension element 66 (as it is wrapped around the second pulley 42).

Figure 1B:
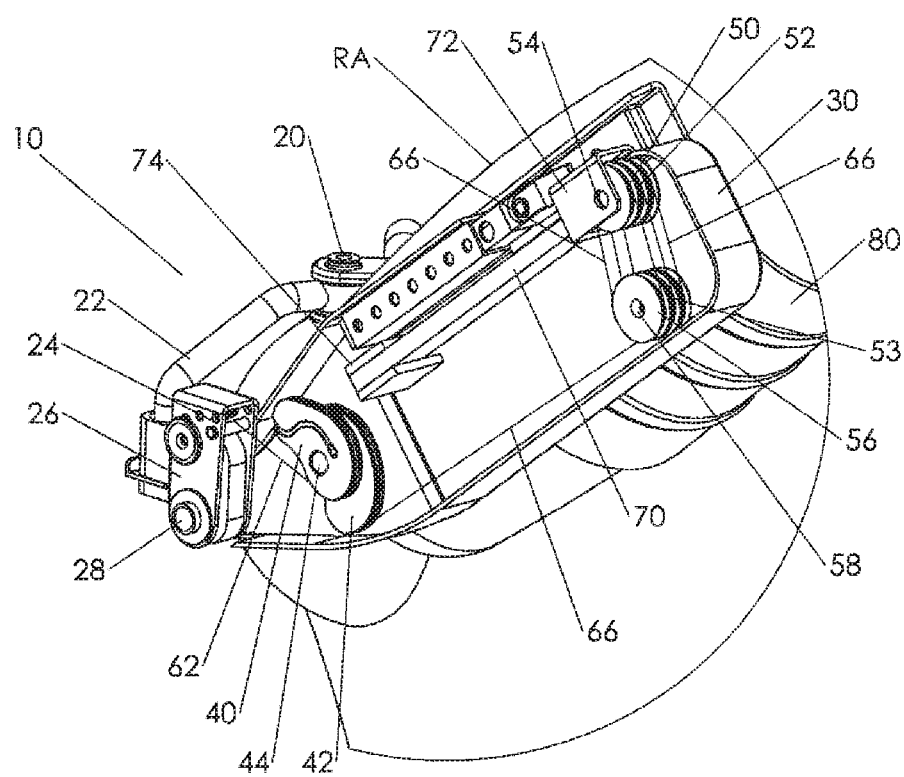
FIGS. 1B and 2B are perspective details of the arm support system shown FIGS. 1A and 2A, respectively.
Figure 3A:
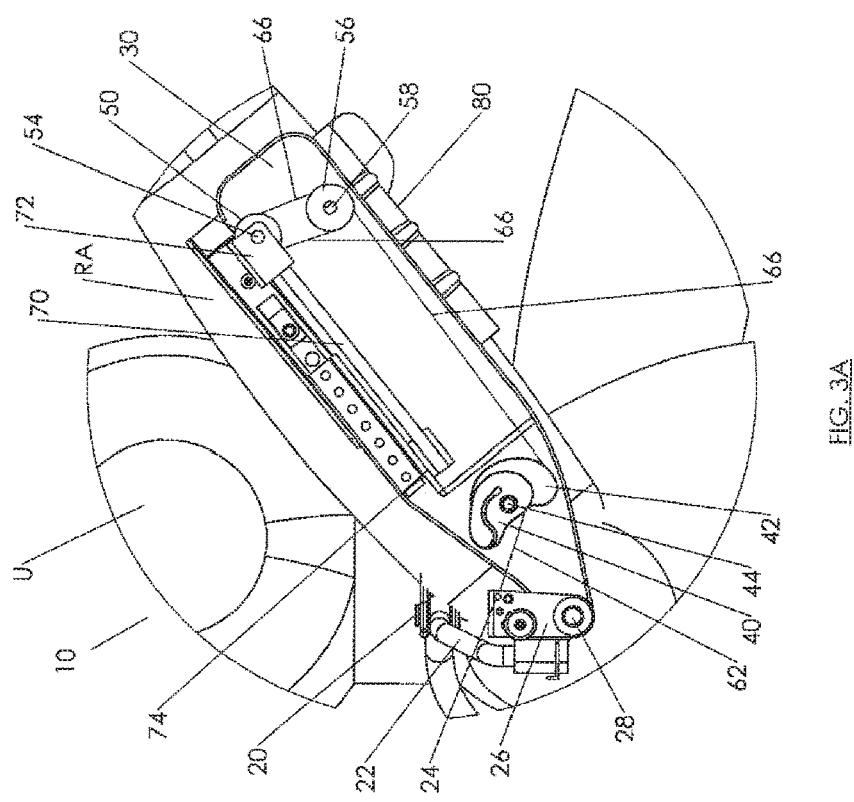

In FIGS. 1B and 3A, the user U's right arm RA is shown raised, and the leaf spring 70 is relatively un-deflected, and the moving pulley(s) 50 are separated from the stationary pulley(s) 56. In this position, the leaf spring 70 provides a lift force on the right arm RA, which is a function of the geometry of the components of the compensation elements, including the radii and sizes of the first pulley 40 and the second pulley 42.

In FIG. 3B, the user U's right arm RA is shown lowered, approximately along arc A1. The leaf spring 70 is relatively deflected, having been pulled toward the stationary pulley(s) 56, and the moving pulley(s) 50 are closer to the stationary pulley(s) 56. The leaf spring 70, substantially deflected in response to the motion of the right arm RA, approximately along path P1, is necessarily imparting greater force in the second tension element 66. However, the greater force in the second tension element 66 is unable to create a greater lift force on the right arm RA because of the geometry of the components, including the radii and sizes of the first pulley 40 and the second pulley 42, which act to negate the increased force of the leaf spring 70 and thus moderate the lift force on the right arm RA, e.g., by "disadvantaging the spring," similar to the embodiments in the applications incorporated by reference herein. It will be appreciated that the geometry of the components may be changed, as desired, to achieve the desired force modification applied to the right arm RA during movement of the arm RA through its normal range of motion.

The leaf spring 70 may be constructed of various metals (e.g., steel), polymers (e.g., Polyacetal), elastomers (e.g., Polyurethane), composites (e.g., carbon fiber structures), and/or natural materials (e.g., wood or bamboo).

Turning to FIGS. 4A-6B, another embodiment of an adaptive arm support system 100 is shown, which includes a harness and arm support, generally similar to other embodiments described with reference to the arm support system 10 of FIGS. 1A-3B and/or as described in the applications incorporated by reference herein. The arm support system 100 differs from the arm support system 10 only in that the leaf spring 110 is deflected in a direction substantially perpendicular to the direction of deflection of the leaf spring 70 shown in FIGS. 1A-3B.

Figure 5B:
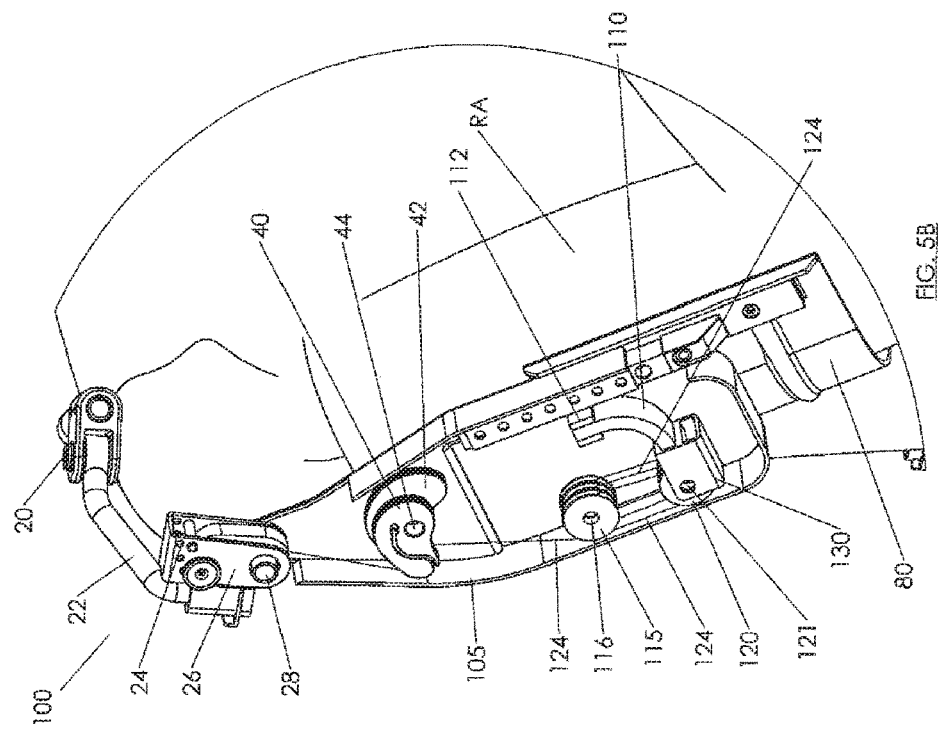
Figure 5A:
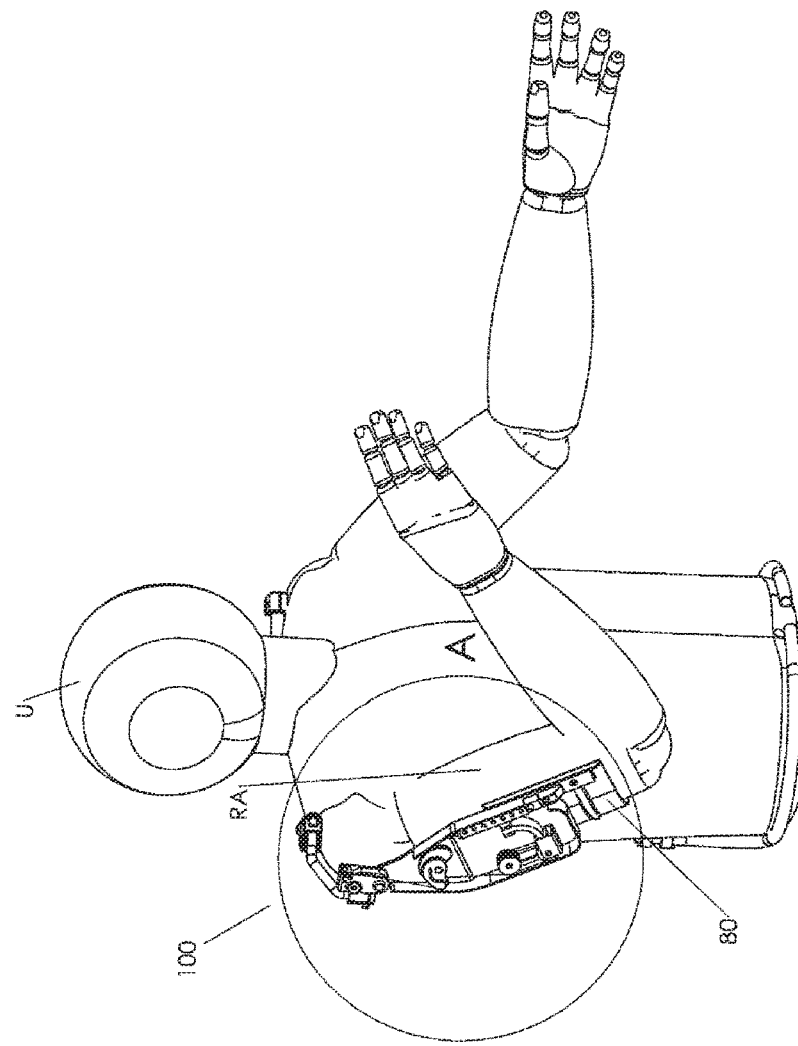

FIG. 4A shows the system 100 with the right arm RA and the arm support raised, while FIG. 5A shows the right arm RA lowered. FIGS. 4B and 6A are details with the arm support raised as in FIG. 4A, while FIGS. 5B and 6B are details with the arm support lowered as in FIG. 5A and provide additional details of a chassis 105 carrying a plurality of components of the compensation elements of the arm support.

In particular, the chassis 105, which rotates about shoulder horizontal pivot 28, provides a mounting structure for several components, as did chassis 30 from FIG. 1A-3B, e.g., including a first pulley 40 and a second pulley 42, which are joined together and rotate as one about axle 44. A first tension element or cable 62 is attached to the first pulley 40 and to an anchor point 24 on hub 26. The first end of the leaf spring 110 is attached to the chassis 105 at cantilever fitting 112. The second, free end of the leaf spring 110 is attached to pulley hub 130, which includes moving axle 121 about which zero, one, or more moving pulleys 120 rotate. One or more stationary pulleys 115 are mounted to the chassis 105 adjacent the moving pulley(s) 120, which are free to rotate about stationary axle 116.

Together the moving pulley(s) 120 and stationary pulley(s) 115 form a "block and tackle" by which force in a second tension element or cable 124 may be amplified by multiplying the number of wraps of the second tension element 124 within the "block and tackle," and thus effectively increasing the number of tension elements working to deflect the leaf spring 110. The first end of the second tension element 124 is attached to the second pulley 42 and wraps about one or more of the moving pulley(s) 120 and stationary pulley(s) 115. The second end of the second tension element 124 may be attached at one of several points, e.g., to the stationary axle 116 or to the moving axle 121. As described previously with reference to FIG. 1B, the number of wraps determine the mechanical advantage of the "block and tackle." For example, if there are three stationary pulleys 115, and two moving pulleys 120, and tension element is attached at moving axle 121, then there are five (5) effective wraps of the second tension element 124 within the "block and tackle," providing a mechanical advantage of five. If, for example, the tension in the second tension element 124 is, at a given point, fifteen kilograms (15 Kg), the total force acting to deflect the leaf spring 110 will be seventy five kilograms (15×5=75 Kg).

FIGS. 5B and 6B are detail of the chassis 105 as shown in FIG. 5A. In response to the user U lowering the right arm RA, the first tension element 62 unwraps from the first pulley 40 and, in response, both the first pulley 40 and the second pulley 42 rotate together about the axle 44. As the second pulley 42 rotates about the axle 44, the second tension element 124 is wrapped farther onto the second pulley 42. This, in turn, tightens the wraps of the second tension element 124 within the "block and tackle," drawing the moving pulley(s) 120 closer to the stationary pulley(s) 115, and deflecting the leaf spring 110 in response. The distance that the moving pulley(s) 120 draws closer to the stationary pulley(s) 115 is a function of the mechanical advantage provided by the number of effective wraps of second tension element 124. For example, if there are five (5) effective wraps of the second tension element 124 within the "block and tackle," the moving pulley(s) 120 may draw closer to the stationary pulley(s) 115 approximately one fifth (⅕) of the change in length of the second tension element 66 (as it is wrapped around the second pulley 42).

In FIG. 6A, the right arm RA is raised, and the leaf spring 110 is relatively un-deflected, and the moving pulley(s) 120 are separated from the stationary pulley(s) 115. The leaf spring 110 provides a lift force on the right arm RA, which is a function of the geometry of the components, including the radii and sizes of the first pulley 40 and the second pulley 42.

In FIG. 6B, the right arm RA is shown lowered approximately along arc A2. The leaf spring 110 is relatively deflected, having been pulled toward the stationary pulley(s) 115, and the moving pulley(s) 120 are closer to the stationary pulley(s) 115. The leaf spring 110, substantially deflected in response to the motion of the right arm RA, approximately along path P2, imparts greater force to the second tension element 124. However, the greater force in the second tension element 124 is unable to create a greater lift force on the right arm RA because of the geometry of the system components, including the radii and sizes of the first pulley 40 and the second pulley 42, which act to negate the increased force of the spring 110, by "disadvantaging the spring," and thus moderate the lift force on the right arm RA. It will be appreciated that the geometry of the components may be changed, as desired, to achieve the desired force modification applied to the right arm RA during movement of the arm RA through its normal range of motion.

Similar to the previous embodiment, the leaf spring 110 may be constructed using various materials and/or methods, e.g., one or more metals (e.g., steel), polymers (e.g., Polyacetal), elastomers (e.g., Polyurethane), composites (e.g., Carbon fiber structures), and/or natural materials (e.g., wood or bamboo).

Figure 7A:
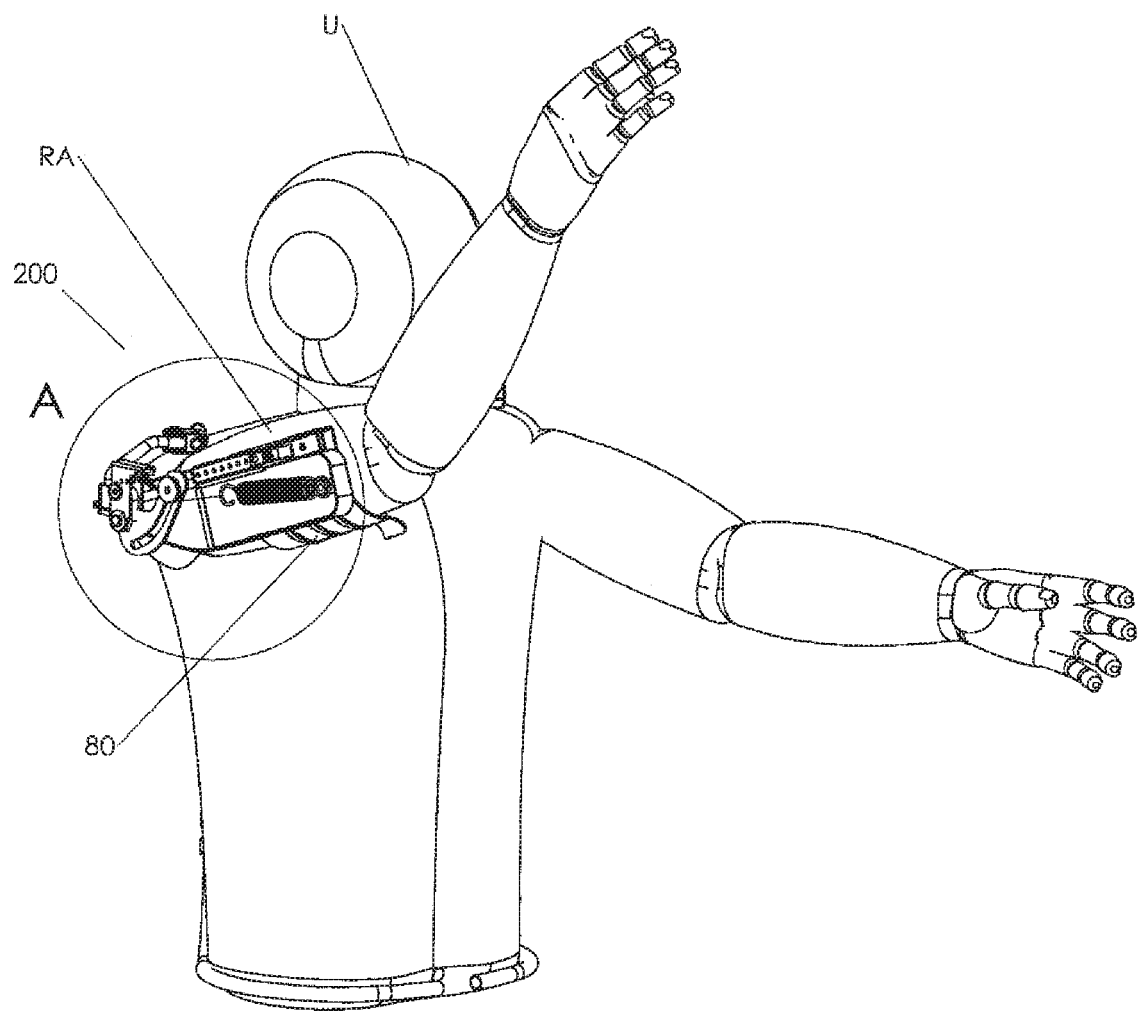
FIGS. 7A and 8A are perspective views of yet another exemplary embodiment of an arm support system worn by a user to support the user's right arm, showing the user's arm raised and lowered, respectively.

Turning to FIGS. 7A-9B, another embodiment of an adaptive arm support system 200 is shown that also includes a harness and an arm support supporting one or both of the user's arms (only the right arm RA shown), generally similar to other embodiments described herein and in the applications incorporated by reference. The harness and shoulder bracket are not shown for clarity. FIG. 7A shows a perspective view of the arm support system 200, with the right arm RA raised, and the arm support acting to provide a lift force on the right arm RA through an armrest 80, while FIG. 8A shows the right arm RA lowered.

Unlike the other embodiments, the arm support system 200 includes a single symmetrical, e.g., circular, pulley 230, that rotates about a moving axle 234 that changes in position, thereby changing the location of the symmetrical pulley 230 and providing a variable offset force between the shoulder bar 22 and the chassis or cartridge 210.

Figure 7B:
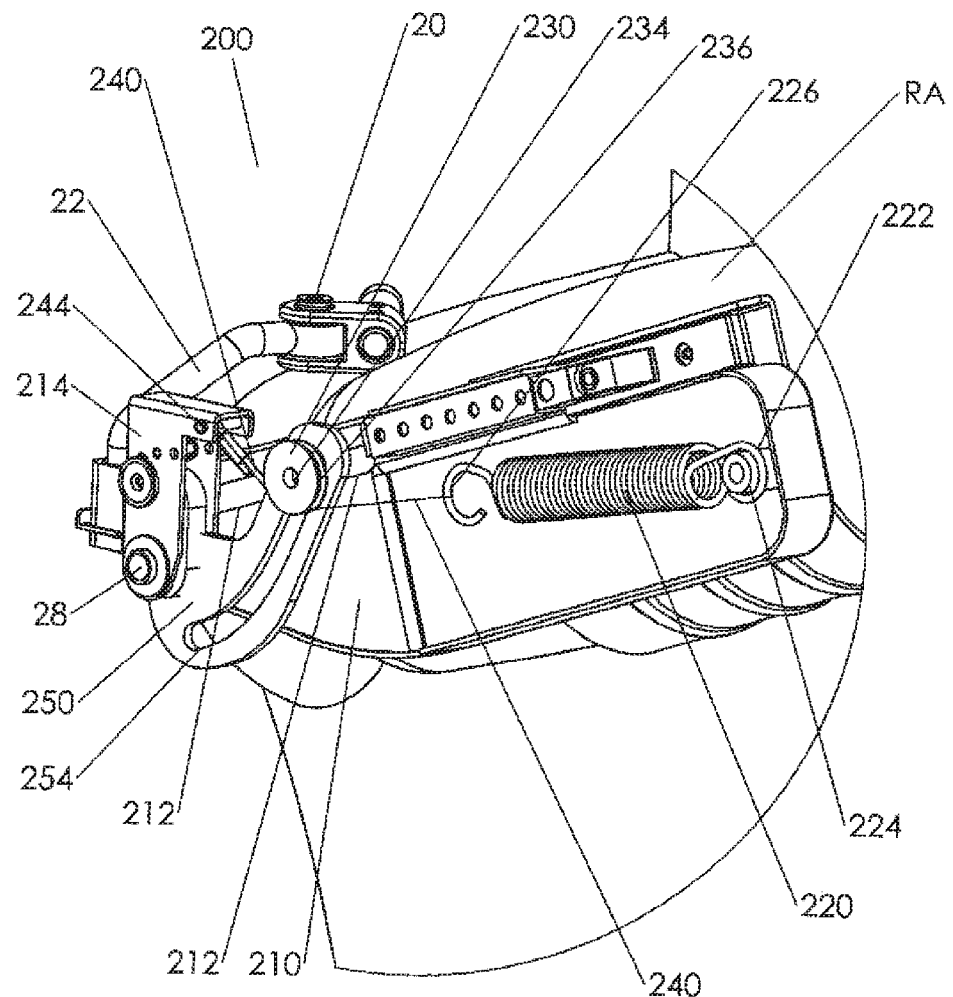
FIGS. 7B and 8B are perspective details of the arm support system shown FIGS. 7A and 8A, respectively.
Figure 8A:
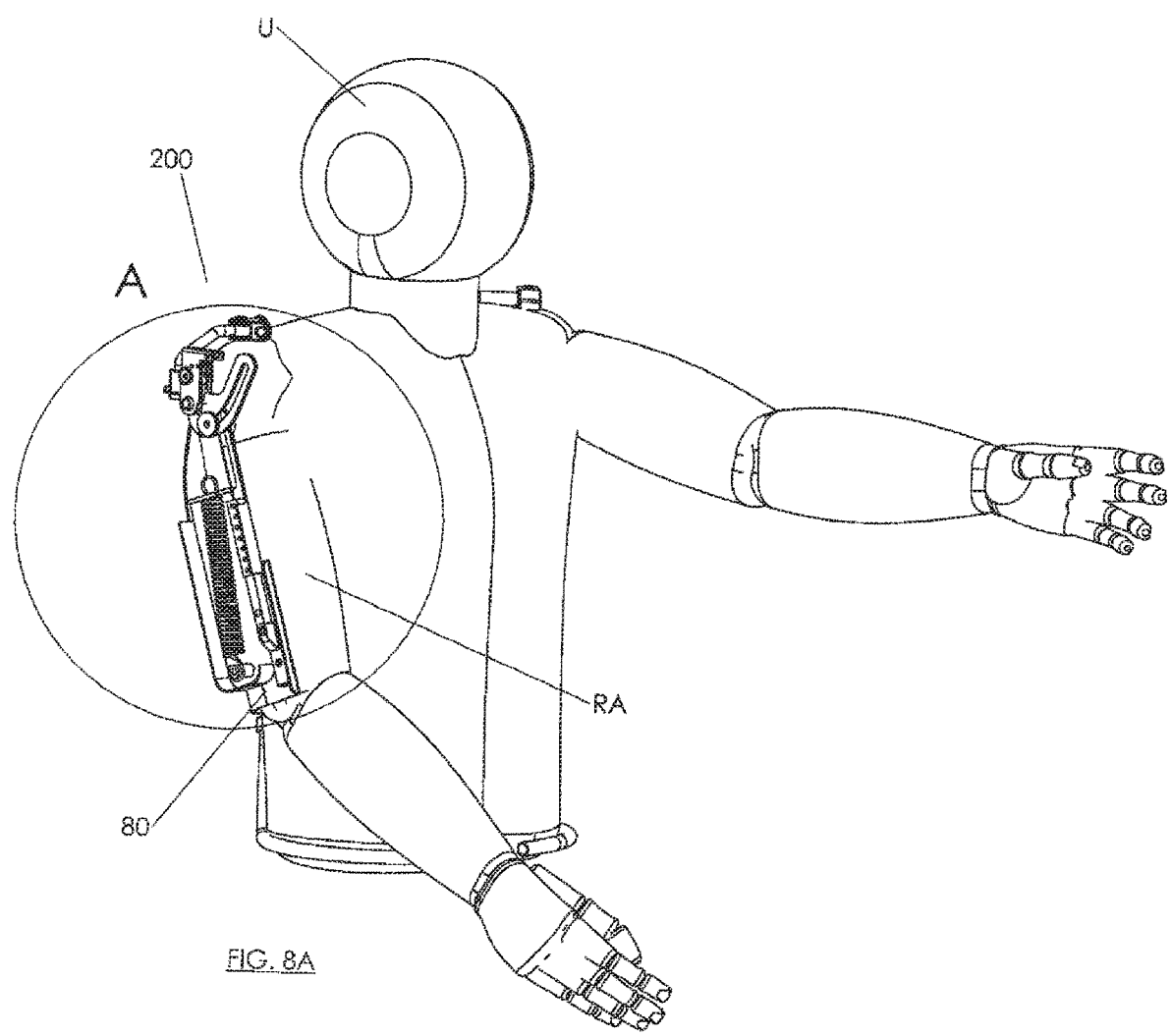
Figure 8B:
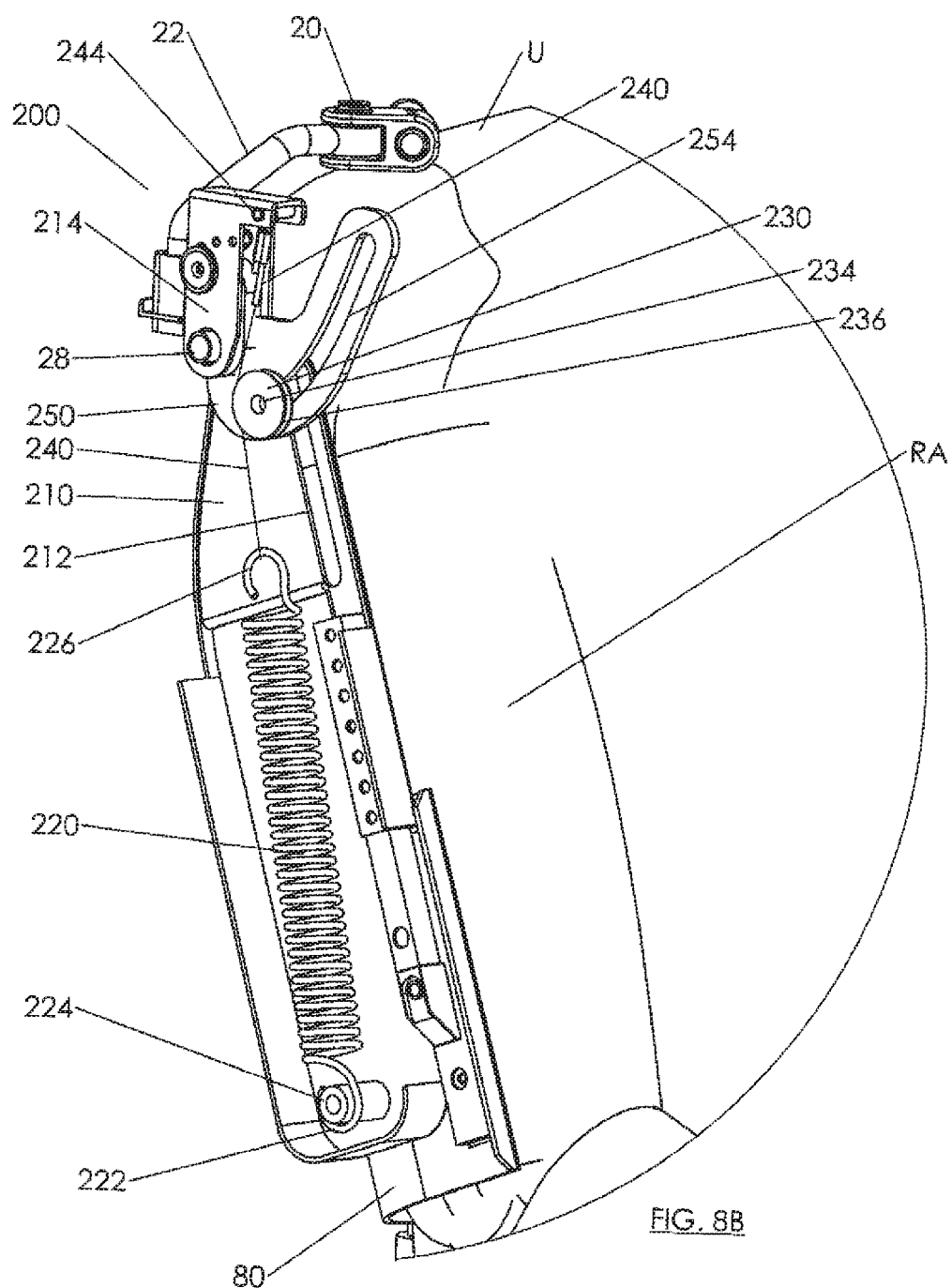
Figure 9B:
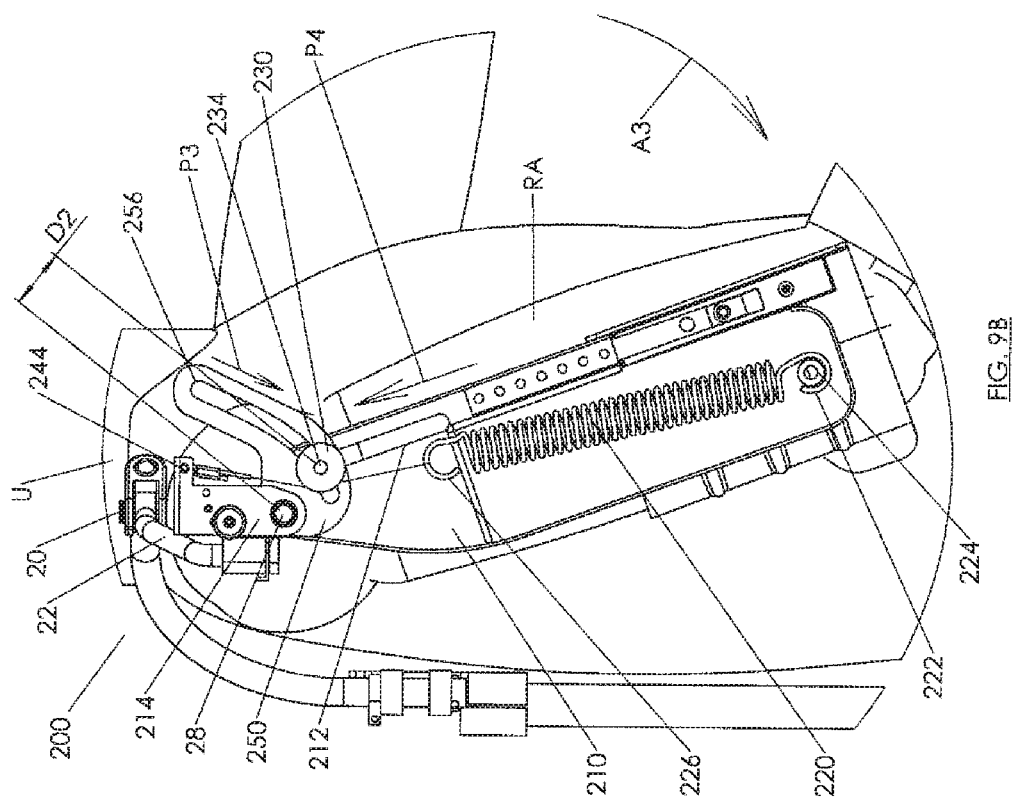
FIGS. 9A and 9B are side view details of the arm support shown in FIGS. 7A and 8A, respectively.
Figure 9A:
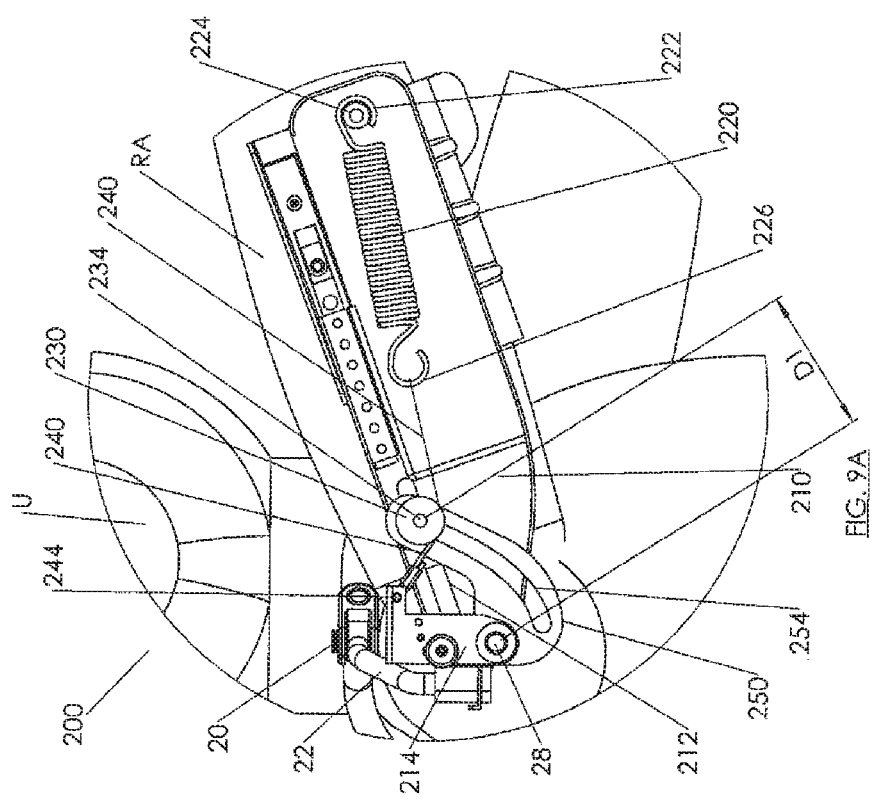

FIGS. 7B and 9A are details of the chassis 210 with the right arm RA raised, and FIGS. 8B and 9B are details of the chassis 210 with the right arm RA lowered, thereby showing the changing configuration of the compensation elements as the right arm RA is raised and lowered.

As in other embodiments, a shoulder vertical pivot 20 may permit rotation of the arm support of the arm support system 200 about a substantially vertical axis. The shoulder bar 22 connects the shoulder vertical pivot 20 to a hub 214, which includes shoulder horizontal pivot 28, enabling rotation about a substantially horizontal axis, similar to other embodiments herein. The chassis 210 rotates about the shoulder horizontal pivot 28, and provides a mounting structure for several components of the compensation element. For example, a first end of a spring or other resilient element 220 connects to the chassis 210, via attachment element 222, at post 224. The second end of the resilient element 220 connects to a tension element or cable 240 via a hook or other attachment element 226. The tension element 240 wraps around the pulley 230 and is attached to the hub 214 at anchor point 244. The pulley 230 rotates about the moving axle 234, which may translate along a slot 212 in the chassis 210, thereby changing the position of the pulley 230 and the distance between the pulley 230 and the shoulder horizontal pivot 28.

A cam plate 250 is fixedly connected to the hub 214 (and consequently to the shoulder bar 22), and includes a cam slot 254, within which the moving axle 234 may also translate. As explained below, the cam slot 254 determines the translation of the moving axle 234, and thus the pulley 230, within the slot 212 in the chassis 210. Thus, by changing the position of the pulley 230, the influence of the resilient element 220, and thus the lift force on the right arm RA, may be controlled. For example, if the resilient element 220 is relatively un-deflected (i.e., retracted) as shown in FIGS. 7B and 9A, it will have less ability to apply a lift force to the right arm RA. However, if the position of the pulley 230 is at the same time relatively far from the shoulder horizontal pivot 28, the influence of the tension element 240 (attached to the hub 214 at anchor point 244, and transmitting the force in the resilient element 220) on the right arm RA is increased.

In response to the user U lowering right arm RA, as shown in FIGS. 8A, 8B, and 9B, the moving axle 234, which is guided by the cam slot 254, has translated within the slot 212 in the chassis 210, thereby translating the pulley 230 relative to the cam slot 254. The position of the pulley 230 closer to the shoulder horizontal pivot 28 (as contrasted with the position of the pulley 230 in FIGS. 7A, 7B, and 9A), results in a shorter moment arm (lever) over which the tension element 240 (and thus the resilient element 220, which is now extended, and therefore applying a higher force to the tension element 240) can act on the right arm RA.

As shown in FIG. 9A, the right arm RA is raised, and the resilient element 220 is relatively un-deflected, and the pulley 230 (carried on the moving axle 234 guided by the cam slot 254, and which has translated within the slot 212 in the chassis 210) is displaced from the shoulder horizontal pivot 28 by distance D1.

In FIG. 9B, the right arm RA is lowered approximately along arc A3, and the resilient element 220 is relatively deflected. The moving axle 234, guided by the cam slot 254, has translated within the cam slot 254 along path P3, and has translated within the slot 212 in the chassis 210 along path P4. The pulley 230, carried on the moving axle 234, is now displaced from the shoulder horizontal pivot 28 by distance D2, which is generally less than the distance D1 (of FIG. 9A). The position of the pulley 230, closer to the shoulder horizontal pivot 28 (as contrasted with the position of the pulley 230 in FIGS. 7A and 7B), results in a shorter moment arm (lever) over which the tension element 240 (and thus the resilient element 220, which is now extended, and therefore applying a higher force to the tension element 240) can act on the right arm RA (thereby "disadvantaging the spring").

The cam slot 254 may be configured to modify the position of the pulley 230 relative to the shoulder horizontal pivot 27, as desired. For example, the cam slot 254 may be shaped to maximize the distance of the pulley 230 from the shoulder horizontal pivot 28 when the right arm RA is raised and the resilient element 220 is applying relatively little force (thereby increasing the net lift force acting on the right arm RA), and to minimize the distance of the pulley 230 from the shoulder horizontal pivot 28 when the right arm RA is lowered and the resilient element 220 is applying greater force (thereby decreasing the net lift force acting on the right arm RA). The shape of the cam slot 254 may create various lift force profiles. An example of a desirable lift profile may be to maximize the lift force when the right arm RA is raised, consistent with working overhead, and to have the lift force reduced to a low level when the right arm RA is lowered, consistent with resting with the right arm RA by the user's side. In another example, the cam slot 254 may be configured to apply a consistent lift force through a specific range of arm position, but to apply no lift above or below that range. Many lift profiles may be achieved by varying the shape of the cam slot 254.

Figure 10A:
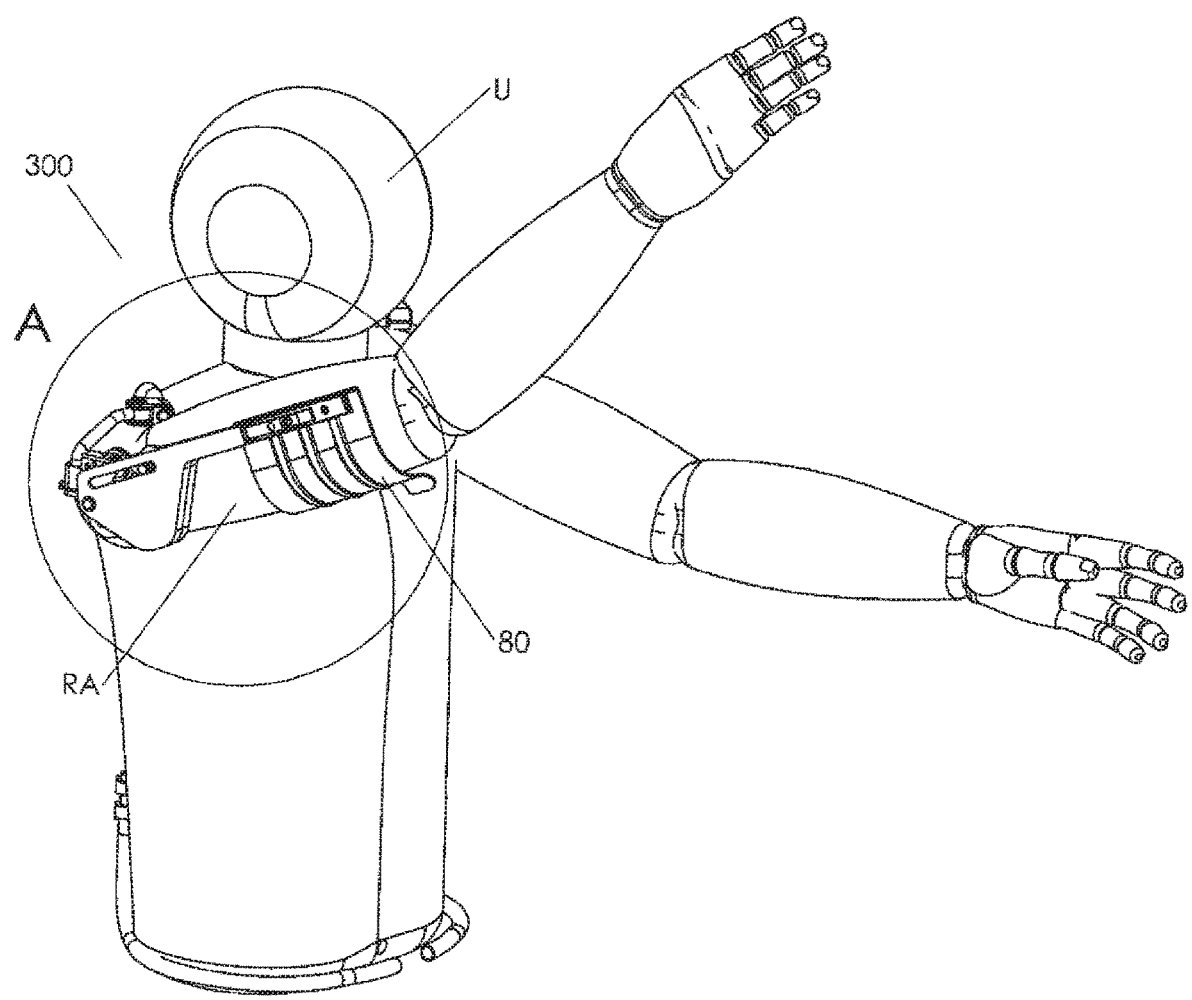
FIGS. 10A and 11A are perspective views of still another exemplary embodiment of an arm support system worn by a user to support the user's right arm, showing the user's arm raised and lowered, respectively.

Turning to FIGS. 10A-12B, another exemplary embodiment of an adaptive arm support system 300 is shown that generally includes a harness worn by a user U and one or two arm supports (one shown supporting a right arm RA of the user U), e.g., including a shoulder bracket 22 and chassis 320 carrying one or more compensation elements, similar to other embodiments herein. FIG. 10A shows a perspective view of the arm support system 300, acting to provide a lift force on the right arm RA through an armrest 80 with the right arm RA shown raised, while FIG. 11A shows the right arm RA lowered.

As with other embodiments, a shoulder vertical pivot 20 may permit rotation of the shoulder bracket 22 of the arm support system 300 about a substantially vertical axis. For example, the shoulder bar 22 connects the shoulder vertical pivot 20 to a hub 310, which includes a shoulder horizontal pivot 28, enabling rotation of the chassis 320 about a substantially horizontal axis, while a resilient torsion element 350 acts to provide a lift force on the right arm RA. In addition, a cam plate 340 is rigidly attached to the hub 310 that includes a cam slot 342 defining a desired curvilinear path for a moving axle 356 to modify the force applied by the torsion element 350 on the right arm RA, as explained further below.

The chassis 320 and cover 330 also include one or more slots, e.g., including outer slot 334 and inner slot 322 (shown in 11B) within which the moving axle 356 also translates, e.g., in combination with the cam slot 342 in the cam plate 340 to vary the position of the moving axle 356 as the right arm RA is raised and lowered, as described below.

Figure 10B:
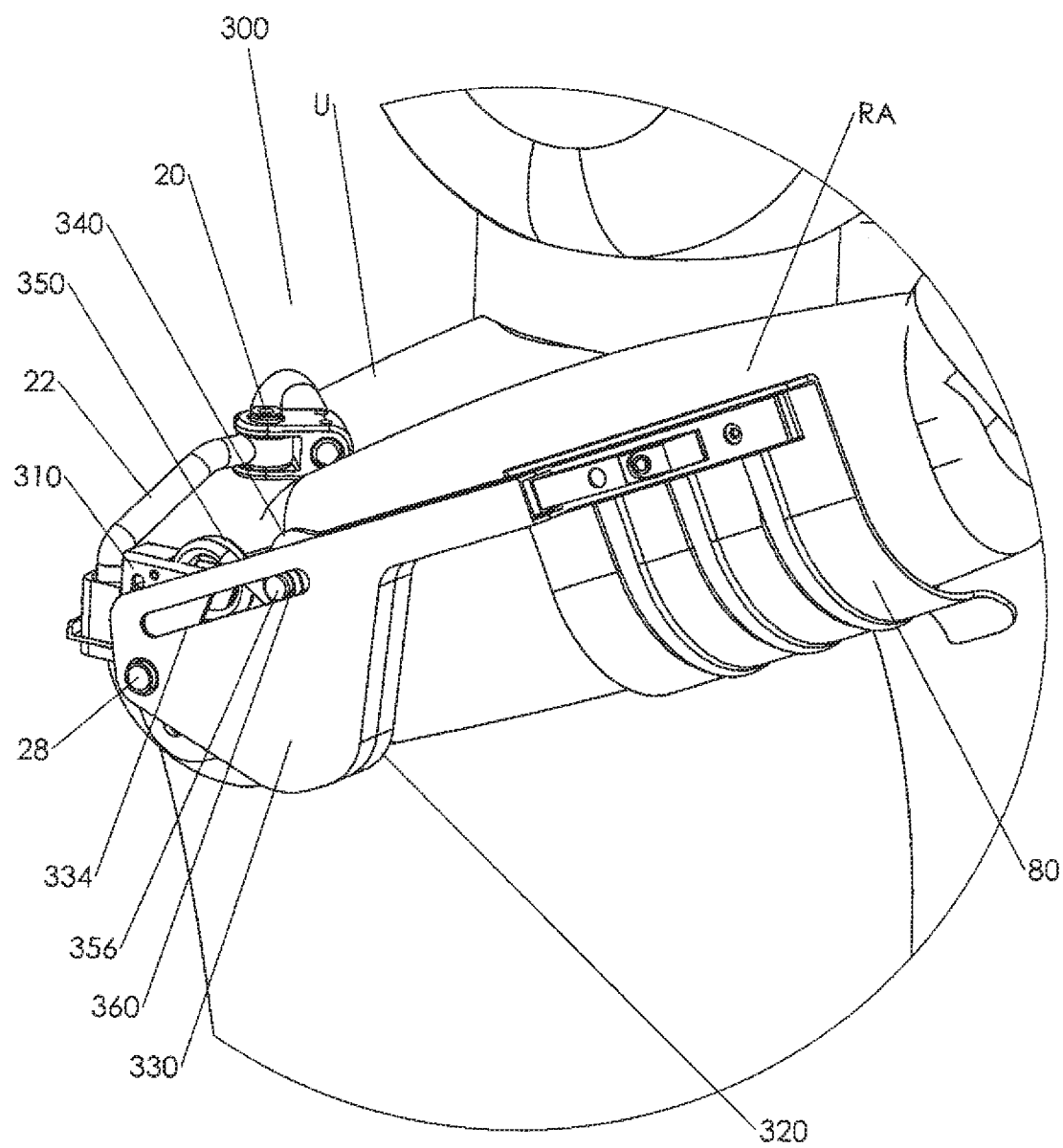
FIGS. 10B and 11B are perspective details of the arm support system shown FIGS. 10A and 11A, respectively.
Figure 11A:
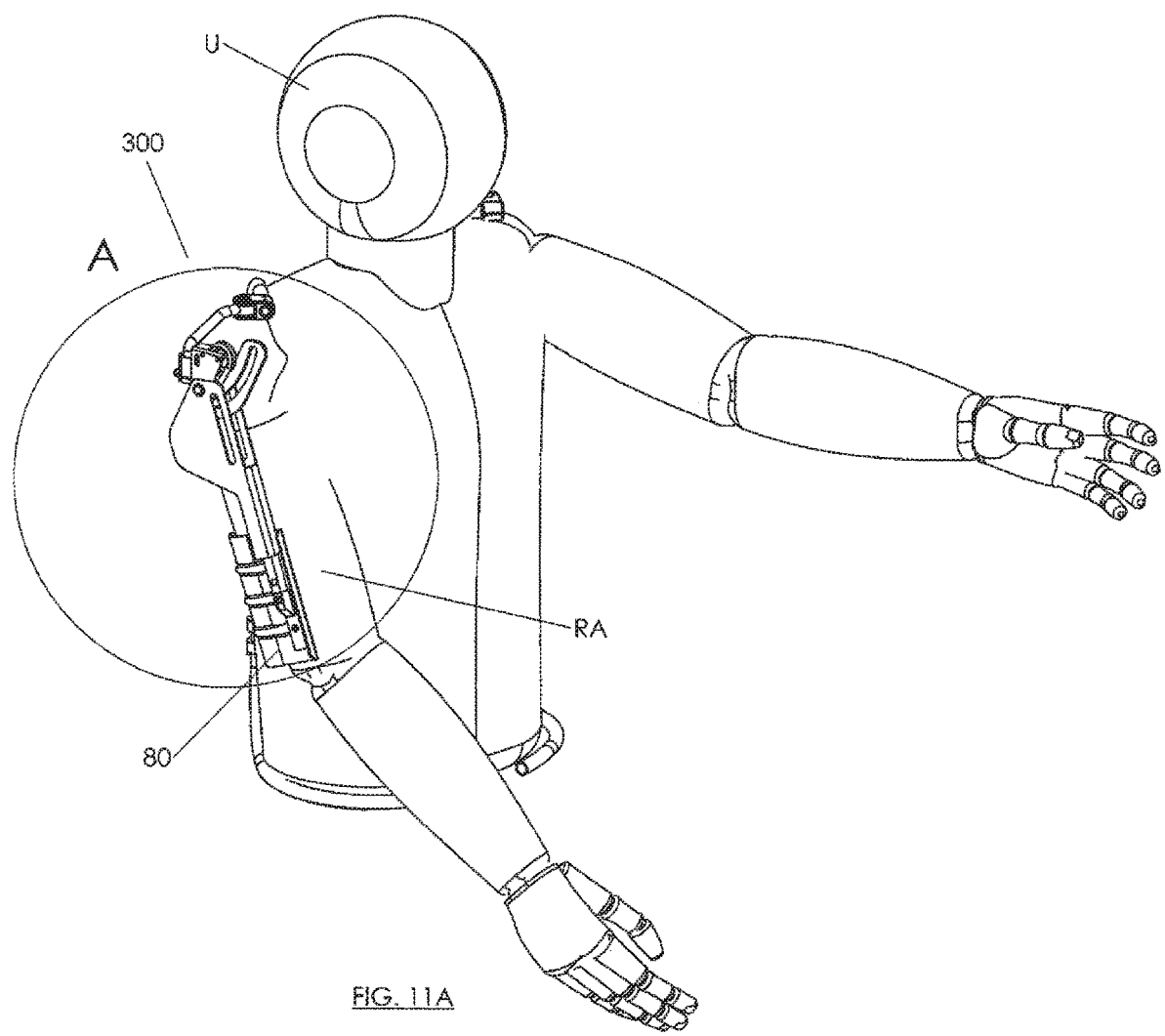
Figure 11B:
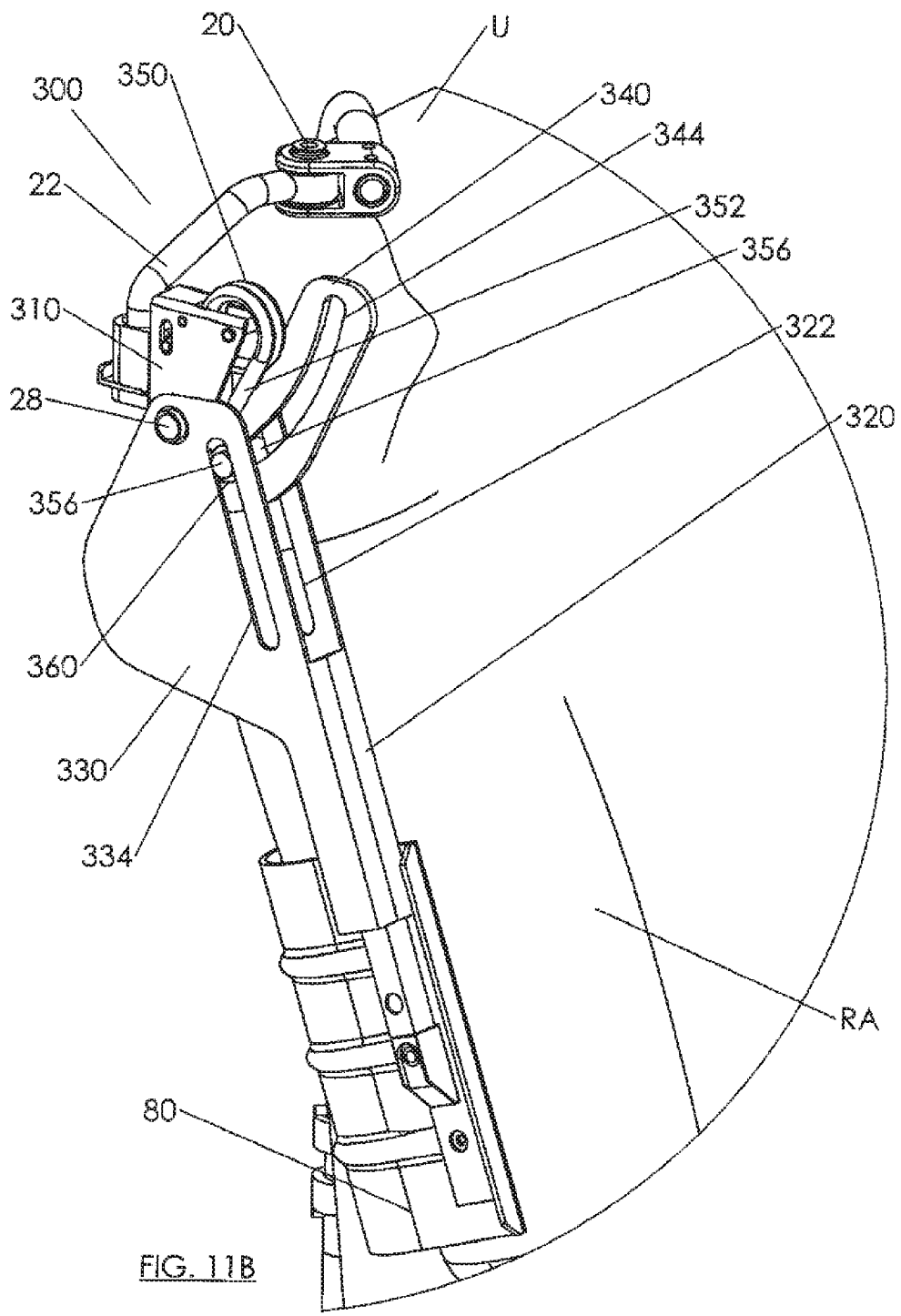

FIGS. 10B and 11B are details corresponding to FIGS. 10A and 11A, respectively, and FIGS. 12A and 12B show side views of FIGS. 10B and 11B, respectively, with a cover 330 of the chassis 320 removed to show components of the compensation elements. In an exemplary embodiment, best seen in FIGS. 12A and 12B, the resilient torsion element 350 is a torsion spring with legs 352, 354. Alternatively, other resilient elements may be provided, e.g., an extension spring, as shown in FIGS. 13A-15B. As best seen in FIGS. 12A and 12B, a first or moving leg 352 of the spring 350 is constrained by and/or coupled to a roller 360 on the moving axle 356 and a second or stationary leg 354 of the spring 350 is constrained by and/or coupled to the hub 310.

Operation of the arm support system 300 is shown in FIGS. 11A-12B. For example, in response to the user U lowering the right arm RA, as shown in FIGS. 11B and 12B, the moving axle 356, guided by the cam slot 344, has translated within the slots 322 and 334 in the chassis 320 and cover 330, carrying with it a roller 360. The position of the roller 360, closer to the shoulder horizontal pivot 28 (as contrasted with the position of the roller 360 in FIGS. 10B and 12A), results in a shorter moment arm (lever) over which the resilient torsion element 350 (which is now deflected, and therefore applying a higher force to the roller 360), can act on the right arm RA (thereby "disadvantaging the spring").

In FIGS. 10B and 12A, the right arm RA is shown raised, the resilient torsion element 350 is relatively un-deflected, and the roller 360 (carried on the moving axle 356 and therefore guided by the cam slot 344 and translating along the slot 322, 334) is displaced from the shoulder horizontal pivot 28 by distance D6. The roller 360 is in contact with the moving leg 352 of the resilient torsion element 350 at distance D5 from the center 312 of the torsion element 350. The stationary leg 354 of the torsion element 350 is in stationary contact with the hub 310.

In FIG. 12B, the right arm RA is lowered (approximately along arc A4). The resilient torsion element 350 is more deflected (in contrast to the deflection at the raised position of FIG. 12A). The moving axle 356 has travelled within the cam slot 344 approximately along path P5, and has simultaneously translated within the slots 322, 334 in the chassis 320 and cover 330 under the guidance of the cam slot 344, approximately along path P6. The roller 360, carried on the moving axle 356, is displaced from the shoulder horizontal pivot 28 by distance D8, and is in contact with the moving leg 352 of the torsion element 350 at distance D7 from the center 312 of the torsion element 350. Because distance D7 is greater than distance D5, the roller 360 has a greater mechanical advantage on the torsion element 350 in the lowered position than it does in the raised position. Because distance D6 is greater than distance D8, the roller 360 has a lower mechanical advantage on the chassis 320 in the lowered position than it does in the raised position. The combination of greater mechanical advantage of the roller 360 over the torsion element 350 and lower mechanical advantage of the roller 360 on the chassis 320 has the result that the increased torsional force in the torsion element 350 (in the lowered position) is unable to increase the lift force on the right arm RA.

The size and/or shape of the cam slot 344 may be configured, as desired, to modify the position of the roller 360 as it travels along the cam slot 344 to provide a desired lift force profile. For example, the cam slot 344 may be shaped to maximize the distance of the roller 360 from the shoulder horizontal pivot 28 when the right arm RA is raised (e.g., as in FIG. 10A) and the torsion element 350 is applying relatively little force, and to minimize the distance of the roller 360 from the shoulder horizontal pivot 28 when the right arm RA is lowered (e.g., as in FIG. 11A) and the torsion element 350 is applying greater force.

An example of a desirable lift profile might be to maximize the lift force when the right arm RA is raised, consistent with working overhead, or fully extended horizontally, and to have the lift force reduced to a relatively low level when the right arm RA is lowered, consistent with resting with the right arm RA by the user's side. In another example, the cam slot 344 can be configured to apply a consistent lift force through a specific range of arm position, but to apply no lift above or below that range. Many lift profiles can be achieved by varying the shape of the cam slot 344. In an alternative embodiment, the system 300 may be simplified, e.g., by making the roller 356 stationary at a predetermined location on the chassis 320 and omitting the cam plate 340. Although this would be less controllable, the distance of the roller 356 from the pivot 28 would change as the chassis 320 is raised and lowered, thereby moderating the lift force applied to the right arm RA, e.g., reducing the lift force as the right arm RA is lowered.

Figure 13A:
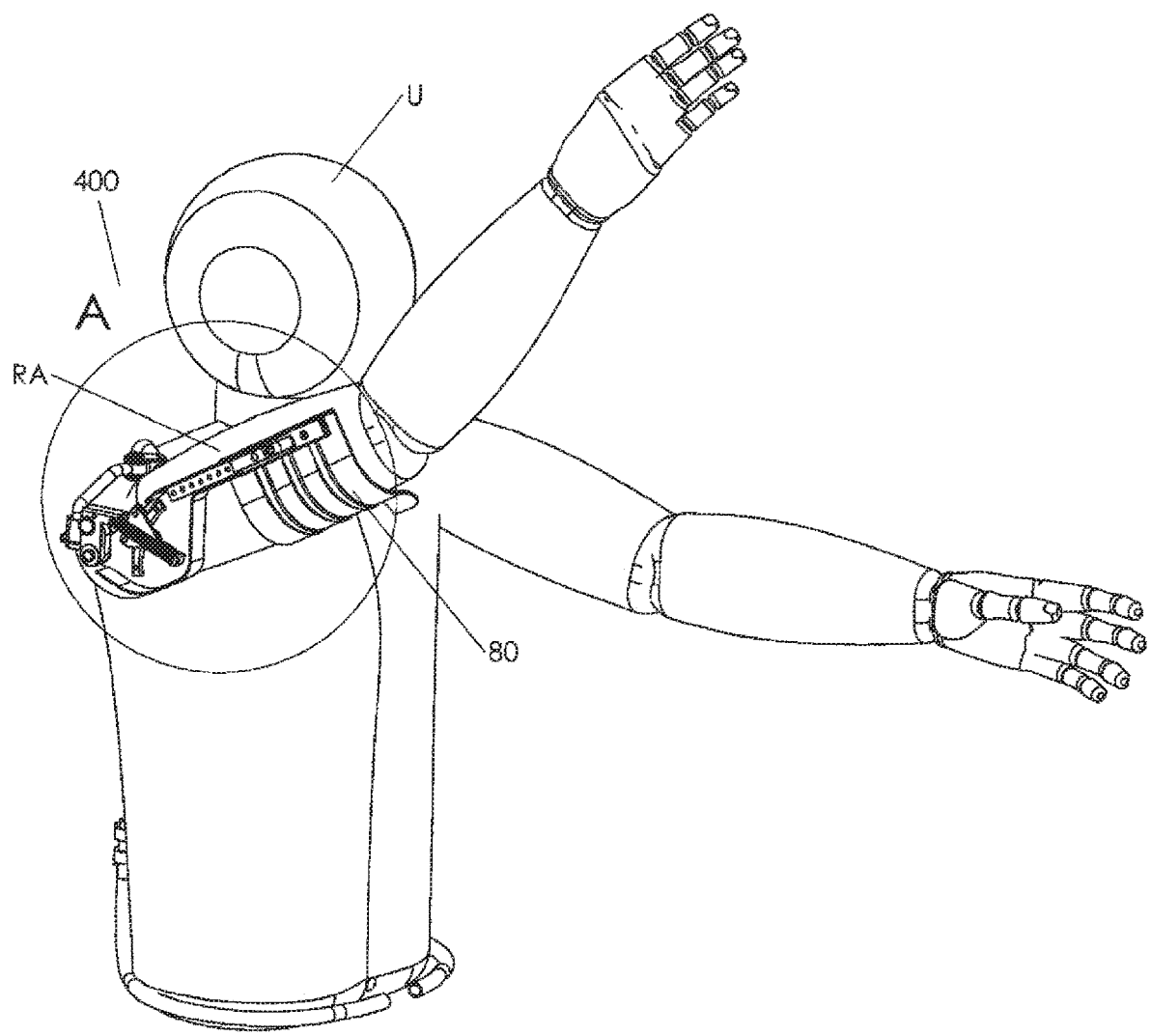
FIGS. 13A and 14A are perspective views of another exemplary embodiment of an arm support system worn by a user to support the user's right arm, showing the user's arm raised and lowered, respectively.

Turning to FIGS. 13A-15B yet another exemplary embodiment of an adaptive arm support system 400 is shown. FIG. 13A shows a perspective view of the arm support system 400, acting to provide a lift force on the right arm RA of a user U through an armrest 80, with the arm support and the right arm RA raised, while FIG. 14A shows the arm support system 400 and the right arm RA lowered. Generally, the system 400 includes a harness (not shown) worn by a user U and an arm support supporting a right arm RA of the user U that includes a shoulder bracket 22 pivotally coupled to the harness, and a chassis 320 pivotally coupled to the shoulder bracket 22 and carrying one or more compensation elements, similar to other embodiments herein.

FIGS. 13B, 14B, 15A, and 15B are details showing components of the compensation elements carried by the chassis 420 (with a cover, not shown, removed), e.g., a spring or other resilient member 460, a curvilinear shaped track 430, and a carriage 440 configured to travel on the track 430. As with other embodiments, a shoulder vertical pivot 20 may permit rotation of the arm support system 400 about a substantially vertical axis, shoulder bar 22 connects the shoulder vertical pivot 20 to a hub 410, which includes a shoulder horizontal pivot 28, enabling rotation about a substantially horizontal axis. The chassis 420 rotates about the shoulder horizontal pivot 28 and provides a mounting structure for a shaped track 430, which rotates with the chassis 420 about the shoulder horizontal pivot 28).

The carriage 440 provides mounting for multiple rollers 446, which follow the shaped track 430, permitting the carriage 440 to translate along the shaped track 430 as desired. In addition, the carriage 440 includes one or more mounting features for one end of the resilient element 460, e.g., a mount arm 450 and a mount tab 454. The mount tab 454 provides an attachment point for a first end of the resilient element 460, e.g., by coupling a hook or other attachment element 462 to the mount tab 454. A second end of the resilient element 460 is coupled to the hub 410, e.g., by coupling a hook or other attachment element 468 to attachment point 414 on the hub 410.

Figure 13B:
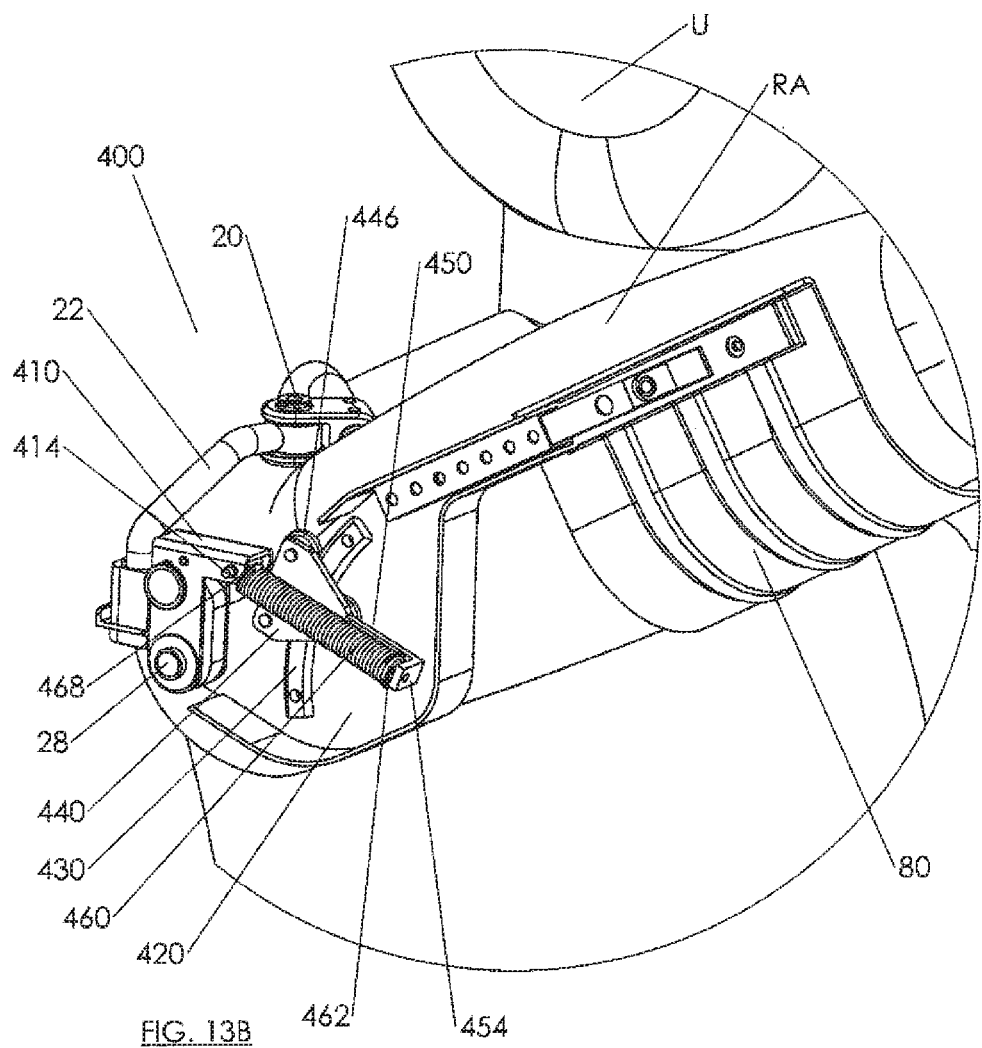
FIGS. 13B and 14B are perspective details of the arm support system shown FIGS. 13A and 14A, respectively.
Figure 14A:
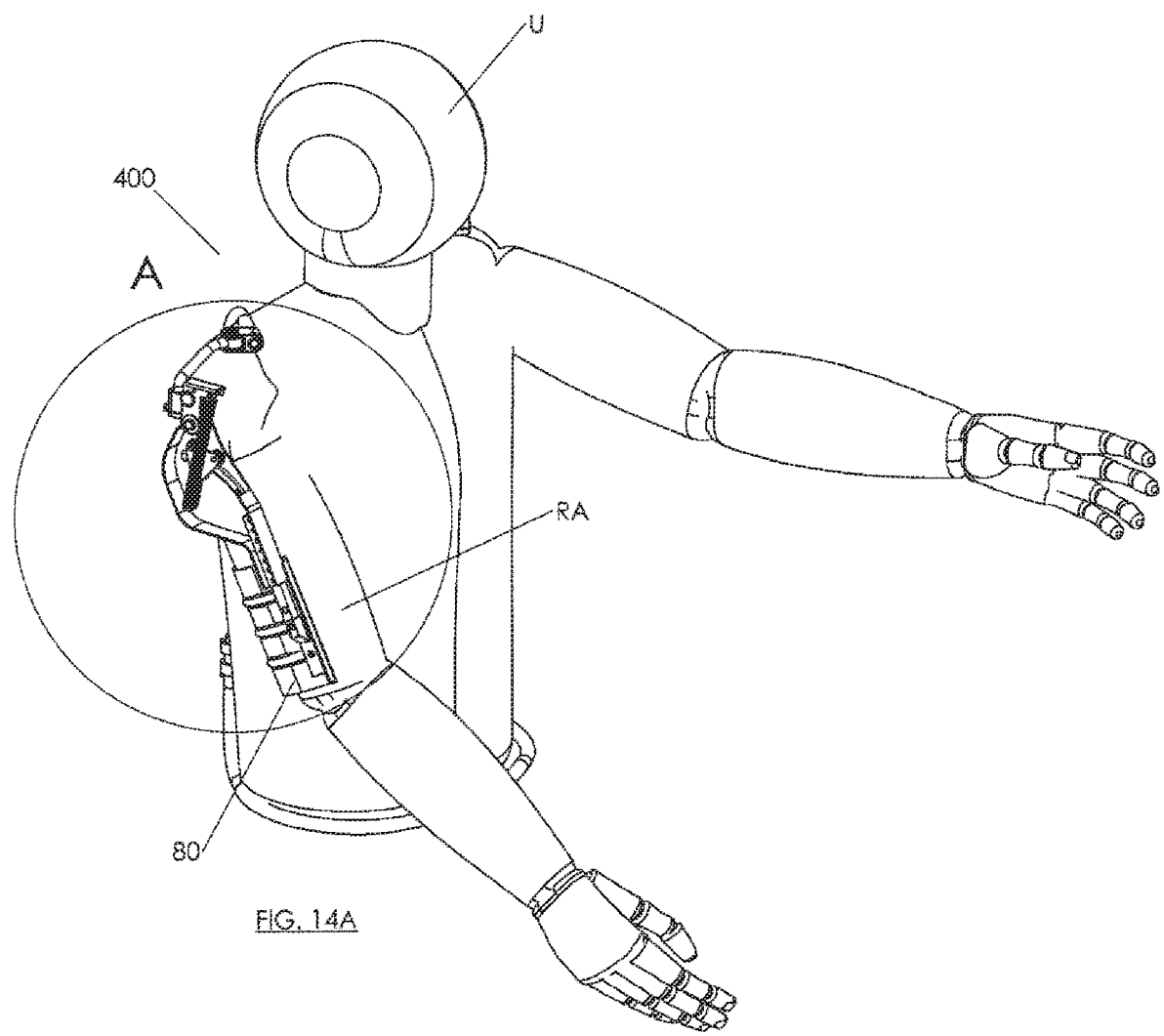
Figure 14B:
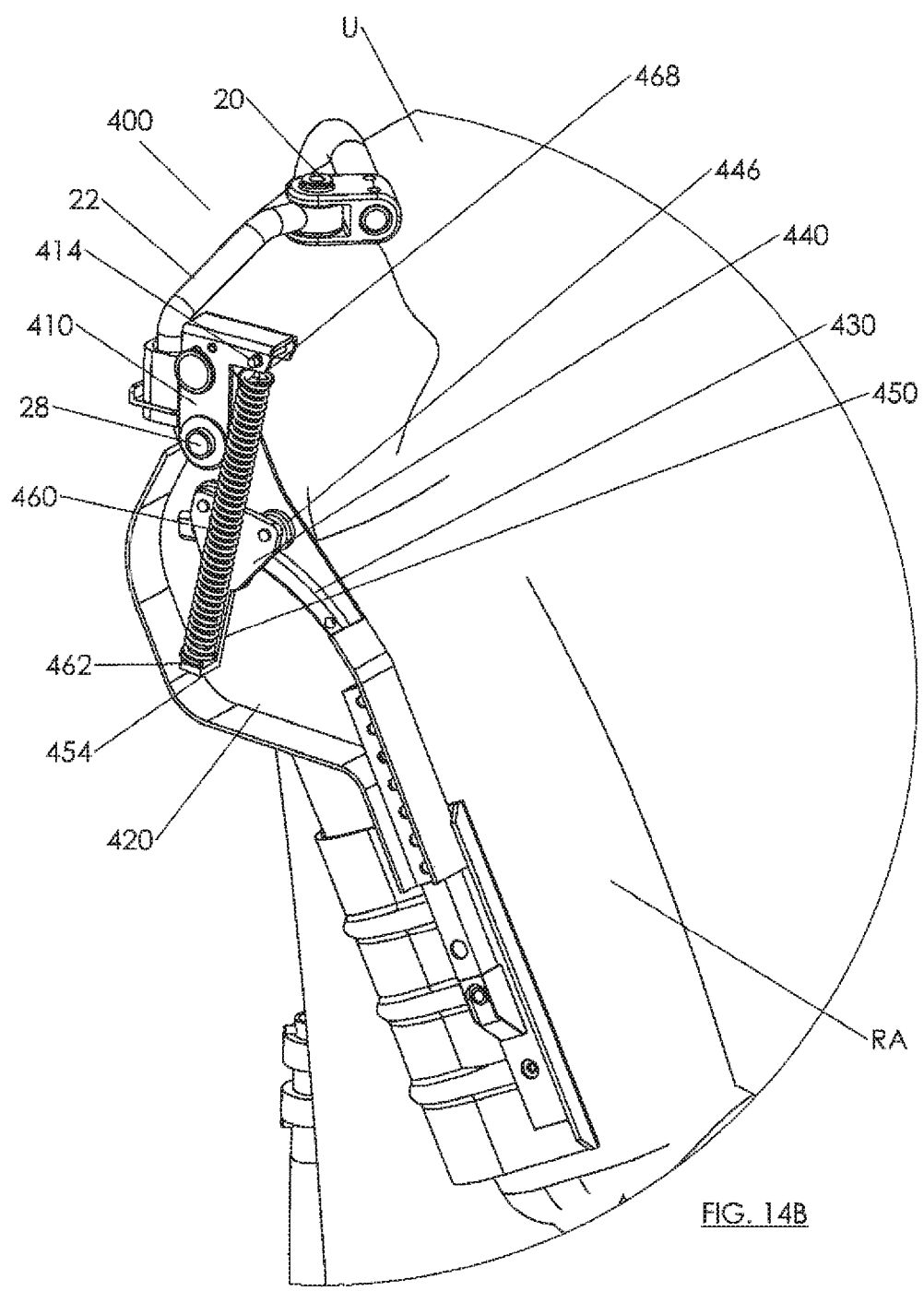

FIGS. 13B and 14B are details corresponding to FIGS. 13A and 14A, respectively, and FIGS. 15A and 15B show side views of FIGS. 13B and 14B, respectively. As shown in FIGS. 13B and 15A, the arm support and right arm RA of the user U are shown raised and the carriage 440 is located towards an outer end 430a of the shaped track 430. FIG. 15A shows the resilient element 460 relatively un-extended, and thus applying a relatively low force on the carriage 440. The carriage 440, however, is located towards the outer end 430a of the track 430 such that the resilient element 460 is acting at distance D9 from the shoulder horizontal pivot 28, and thus the resilient element 460 can provide an adequate lift force on the right arm RA.

FIG. 15B shows user U's right arm RA lowered approximately along arc A5. Resilient element 460 is relatively extended, and thus applying a relatively large force on the carriage 440. In response to user U lowering the right arm RA, the carriage 440 has simultaneously travelled along the shaped track 430, approximately along arc A6, moving closer to the inner end 430b of the track 430 and therefore closer the shoulder horizontal pivot 28. Simultaneously, the resilient element 460 has extended, and, acting at distance D10 from shoulder horizontal pivot 28, is exerting more force on the mount tab 454 and attachment point 414 on the hub 410. D9 being larger than D10, the extended resilient element 460 is acting with less mechanical advantage, and thus does not provide an excessive lift force on the right arm RA (again thereby "disadvantaging the spring"). The shape and/or position of the shaped track 430 may be modified, as desired, to provide a desired profile of lift forces on the right arm RA as it moves up and down, similar to the cam slot 344 described previously.

Figure 16A:
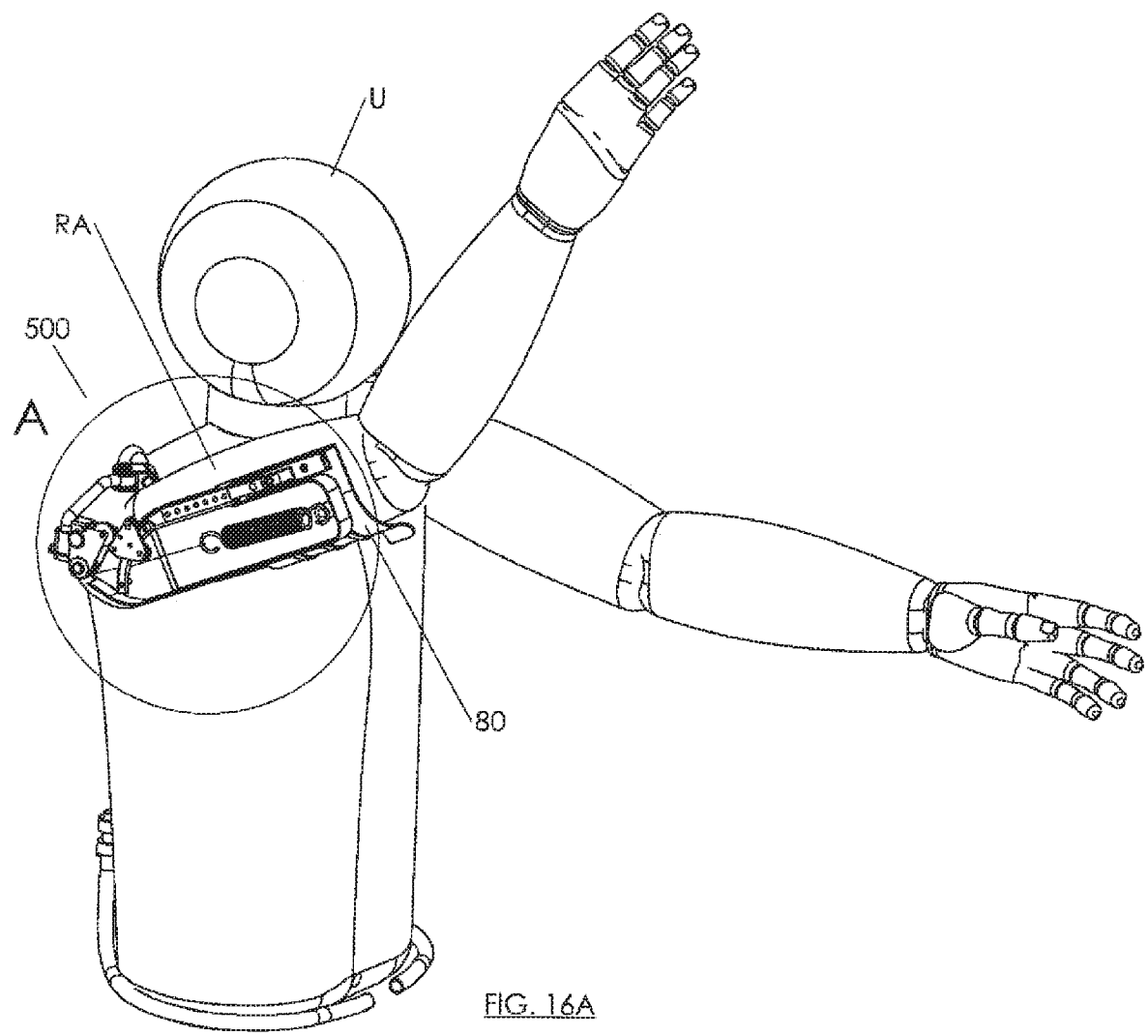
FIGS. 16A and 17A are perspective views of still another exemplary embodiment of an arm support system worn by a user to support the user's right arm, showing the user's arm raised and lowered, respectively.
Figure 16B:
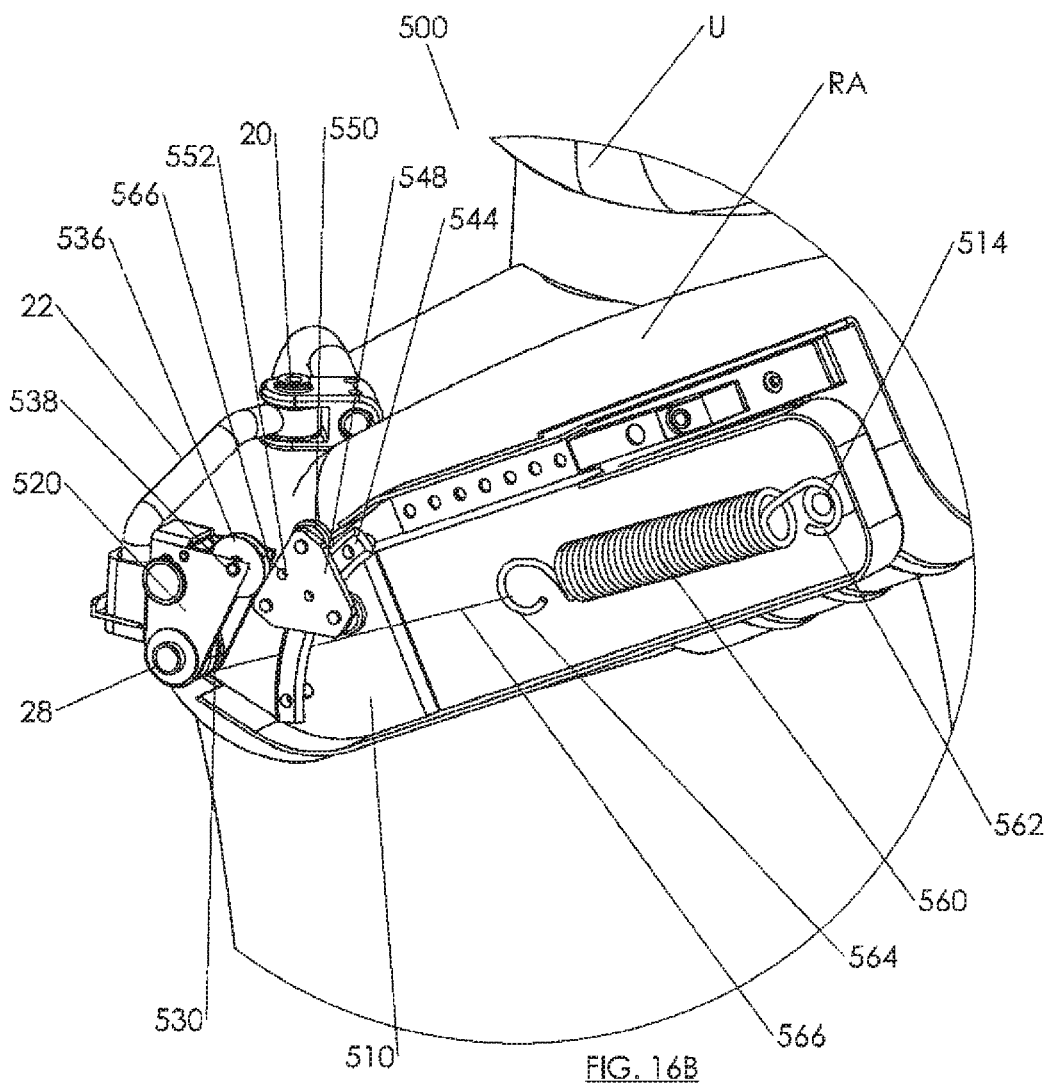
FIGS. 16B and 17B are perspective details of the arm support system shown FIGS. 16A and 17A, respectively.

Turning to FIGS. 16A-18B, still another exemplary embodiment of an adaptive arm support system 500 is shown acting to provide a lift force on a right arm RA of a user U through an armrest 80 as the right arm RA is raised and lowered. In FIG. 16A, the arm support system 500 and the right arm RA are shown raised, while in FIG. 17A, the arm support system and right arm RA are shown lowered. Generally, the system 500 includes a harness (not shown) worn by a user U and an arm support supporting one or both arms of the user U, which includes a shoulder bracket 22 pivotally coupled to the harness, and a chassis 510 pivotally coupled to the shoulder bracket 22 and carrying one or more compensation elements, similar to other embodiments herein.

Unlike the previous embodiments, the arm support 500 employs a pair of symmetrical, e.g., circular, pulleys 530, 536, a curvilinear shaped track 544, and a carriage 548 to change the location of the attachment point of a tension element such as a cable 566, to moderate the lift force on the right arm RA. Other previously disclosed components, such as a frame, shoulder-centered gimbal, and harness are not shown for clarity. For example, as with other embodiments, a shoulder vertical pivot 20 may permit rotation of the arm support system 500 about a substantially vertical axis, shoulder bar 22 connects the shoulder vertical pivot 20 to a hub 520, which includes a shoulder horizontal pivot 28, enabling rotation about a substantially horizontal axis.

The chassis 510, which rotates about shoulder horizontal pivot 28, provides a mounting structure for several components. For example, an extension spring or other resilient element 560 may be coupled between the chassis 510 and the hub 520 to apply a desired lift force on the right RA. As shown, a first end of the resilient element 560 is connected to the chassis 510, e.g., via a hook or other attachment element 562, at post 514. A second end of the resilient element 560 connects to a tension element 644, e.g., via a hook or other attachment element 564. The chassis 510, which rotates about shoulder horizontal pivot 28, provides a mounting structure for the shaped track 544 (which rotates with it about shoulder horizontal pivot 28).

The carriage 548 provides a mounting structure for multiple rollers 550, which follow the shaped track 544, permitting the carriage 548 to translate along the shaped track 544 as desired. A first pulley 530 is mounted within the hub 520, approximately concentric with the shoulder horizontal pivot 28, and a second pulley 536 is mounted within the hub 520 at axle 538. The tension element 560 wraps at least partially around the first pulley 538, the second pulley 536 and is attached to the carriage 548 at anchor point 552.

FIG. 18A shows the resilient element 560 relatively un-extended, and thus applying a relatively low force on the tension element 566 and thus on the attachment point 538 of the carriage 548. The carriage 548, however, is located towards an outer end 544a of the shaped track 544 such that the resilient element 566 is acting at distance D11 from the shoulder horizontal pivot 28, and thus the resilient element 566 can provide an adequate lift force on the right arm RA.

Figure 17A:
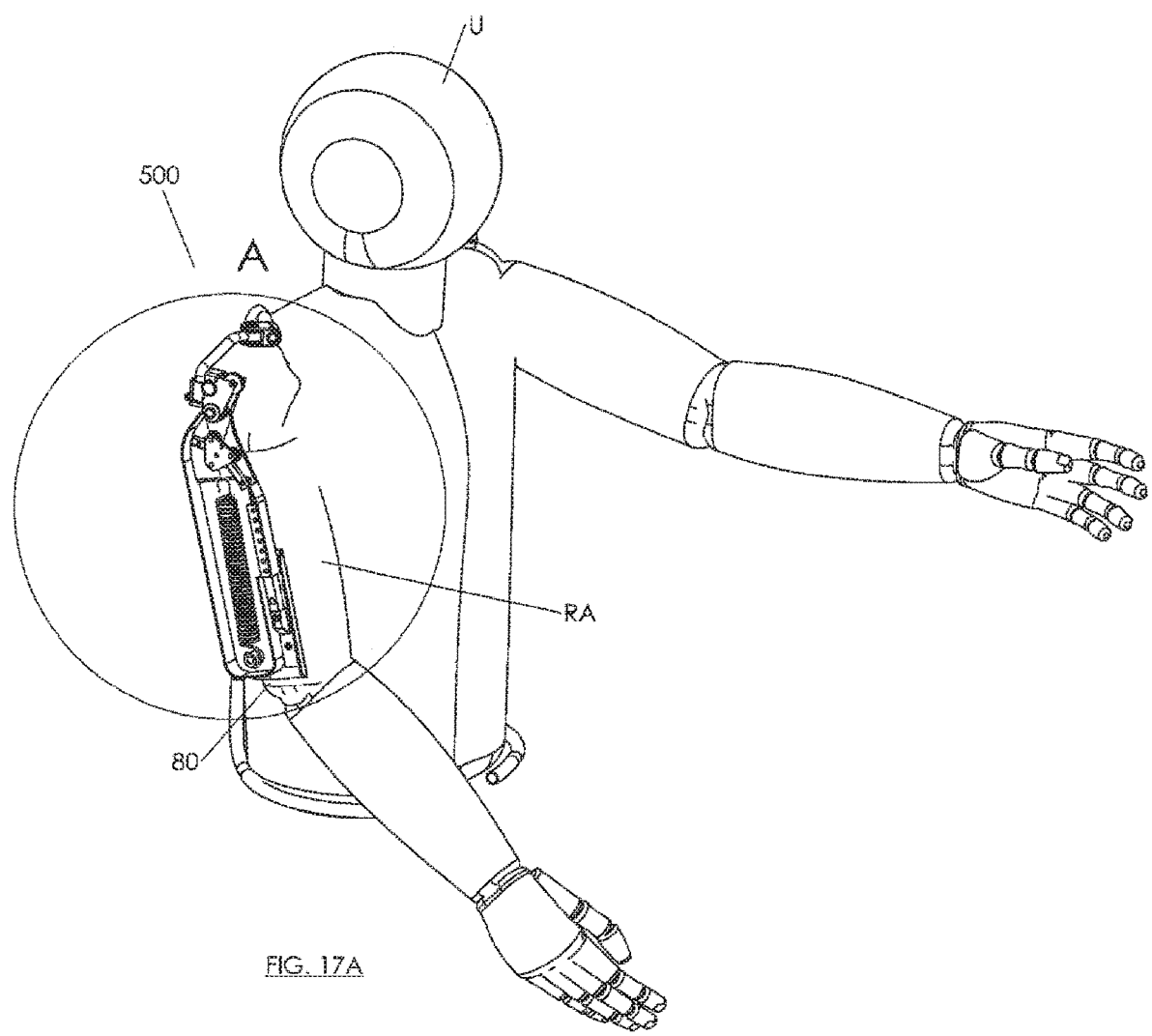
Figure 17B:
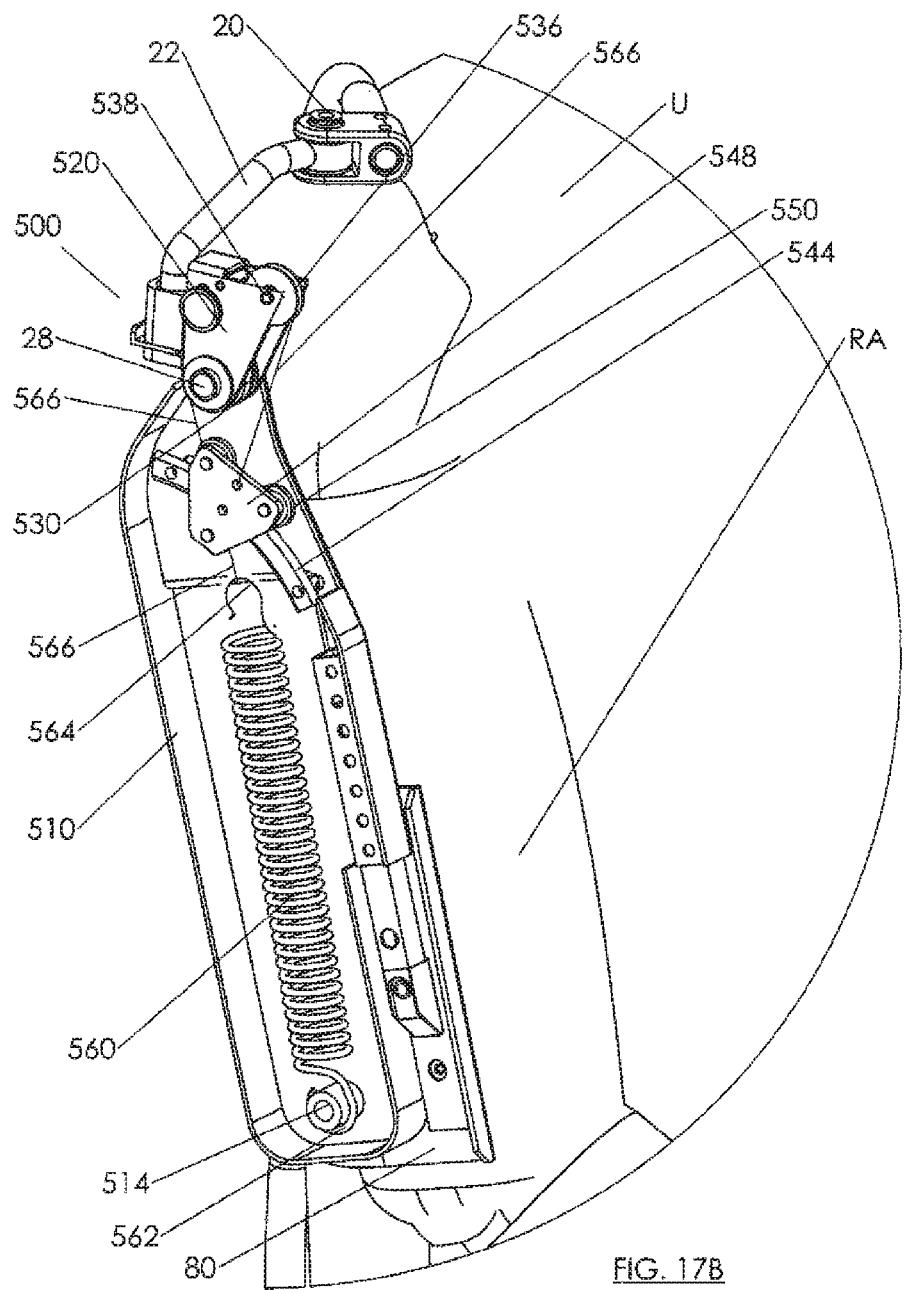

As best seen in FIGS. 17B and 18B, in response to the user U lowering right arm RA, the carriage 548 has travelled along the shaped track 544, moving closer to the shoulder horizontal pivot 28, while simultaneously the resilient element 560 has extended, and is exerting more force on the tension element 560. FIG. 18B shows user the right arm RA lowered approximately along arc A7. The resilient element 566 is relatively extended, and thus applying a relatively large force on the tension element 566 and thus on the attachment point 538 of the carriage 548. The carriage 548 has simultaneously travelled along the shaped track 544, approximately along arc A8, towards an inner end 544b of the shaped track 544, and the resilient element 566 is acting at distance D12 from the shoulder horizontal pivot 28. D11 being larger than D12, the extended resilient element 566 is acting with less mechanical advantage, and thus does not provide an excessive lift force on the right arm RA (again thereby "disadvantaging the spring"). The shape and/or position of the shaped track 430 can be modified, as desired, to achieve the desired profile of lift forces on the right arm RA.

It will be appreciated that elements or components shown with any embodiment herein are merely exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for supporting an arm of a user, comprising:
   a harness configured to be worn on a body of a user;
   an arm support comprising a first arm support segment pivotally coupled to the harness about a first vertical axis such that the first arm support segment is rotatable substantially horizontally about the first vertical axis relative to the harness, and a second arm support segment pivotally coupled to the first arm support segment at a hub such that the second arm support segment is rotatable about a second axis generally orthogonal to the first vertical axis; and
   one or more compensation elements to apply an offset force to at least partially offset a gravitational force acting on the arm as the user moves and the arm support follows the movement of the user's arm, the one or more compensation elements comprising:
      a cam plate fixedly coupled to the hub and including a curvilinear track;
      a moving axle slidably mounted within a chassis slot in a chassis of the second arm support segment, the moving axle slidably disposed within the track of the cam plate such that the moving axle moves along the track and within the chassis slot as the second arm support segment is raised and lowered; and
      a spring including a first fixed end and a second end coupled to the moving axle such that the offset force increases as the moving axle moves along the track away from the second axis and decreases as the moving axle moves along the track towards the second axis.

2. The system of claim 1, wherein the spring comprises an extension spring with the first fixed end mounted to the chassis, the system further comprising:
   a pulley rotatably mounted to the moving axle; and
   a tension element wrapped at least partially around the pulley and including a first end coupled to the second end of the spring and a second end coupled to the hub such that, as the second arm support segment is lowered, the pulley moves towards the second axis as the moving axle moves along the track towards the second axis to reduce the offset force applied by the tension element, and, as the second arm support segment is raised, the pulley moves away from the second axis as the moving axle moves along the track away from the second axis to increase the offset force applied by the tension element.

3. The system of claim 1, wherein the spring comprises a torsion spring with the first fixed end mounted to the hub, and wherein the second end of the spring is coupled to the moving axle such that, as the moving axle moves along the track towards the second axis, the offset force is reduced, and, as the moving axle moves away from the second axis, the offset force is increased.

4. The system of claim 1, wherein the one or more compensation elements are configured to apply a relatively high offset force when the second arm support segment is raised above a horizontal position about the second axis and a relatively low offset force when the second arm support segment is lowered below the horizontal position.

5. A method for supporting an arm of a user during one or more tasks using the system of claim 1, comprising:
   placing a harness on the user, the harness comprising an arm support movable relative to the harness and including an arm rest, the arm support including one or more compensation elements according to claim 1;
   supporting a portion of the user's arm using the arm support such that the arm support subsequently follows movement of the user's arm; and
   performing one or more tasks involving movement of the user's arm, the one or more compensation elements applying the offset force to at least partially offset the gravitational force acting on the arm as the user moves without substantially interfering in the movement, the one or more compensation elements providing a force profile that varies the offset force based on an orientation of the arm support.

6. A system for supporting an arm of a user, comprising:
   a harness configured to be worn on a body of a user;
   an arm support coupled to the harness configured to support an arm of the user, the arm support configured to accommodate movement of the arm while following the movement, the arm support comprising an arm support segment configured to support an upper arm of the user and pivotable about a pivot to follow movement as the upper arm is raised and lowered; and
   one or more compensation elements to apply an offset force to at least partially offset a gravitational force acting on the arm as the user moves and the arm support follows the movement of the user's arm, the one or more compensation elements comprising:
      a cam plate fixedly coupled to the arm support segment and including a curvilinear track;
      a moving axle slidably mounted within the track such that the moving axle moves along the track as the arm support segment is raised and lowered;
      a spring including a first end fixed to the arm support segment and a second end coupled to the moving axle such that the offset force increases as the moving axle moves along the track away from the pivot and decreases as the moving axle moves along the track towards the pivot; and
      a chassis mounted to the arm support segment, the chassis comprising a chassis slot that slidably receives the moving axle, the track and chassis slot cooperating to vary a position of the moving axle within the track as the arm support segment is raised and lowered.

7. The system of claim 6, wherein the spring comprises a torsion spring with the first end mounted to the arm support segment, and wherein the second end is coupled to the moving axle such that, as the moving axle moves along the track towards the pivot, the offset force is reduced, and, as the moving axle moves away from the pivot, the offset force is increased.

8. The system of claim 7, wherein the moving axle carries a roller that follows movement of the moving axle within the track, and wherein the second end of the spring is coupled to the roller to deflect the second end of the spring and modify a torsional force of the spring applied to the arm support segment.

9. The system of claim 6, wherein the curvilinear track has a predetermined shape configured to direct the moving axle closer to the pivot as the arm support segment is raised and further from the pivot as the arm support segment is lowered.

10. The system of claim 6, wherein the curvilinear track has a predetermined shape configured to direct the moving axle closer to the pivot as the arm support segment is raised to reduce a moment arm of a spring force applied by the spring to the arm support segment to increase the offset force, and direct the moving axle further from the pivot as the arm support segment is lowered to increase a moment arm of the spring force to reduce the offset force.

11. The system of claim 6, wherein the curvilinear track has a predetermined shape configured to cause the spring to apply a consistent offset force when the arm support segment is raised above a predetermined arm position and reduce the offset force when the arm support segment is lowered below the predetermined arm position.

12. The system of claim 6, further comprising a cover to at least partially cover the one or more compensation elements.

13. The system of claim 6, wherein the spring comprises an extension spring with the first end mounted to the arm support segment, the system further comprising:

a pulley rotatably mounted to the moving axle; and
a tension element wrapped at least partially around the pulley and including a first end coupled to the second end of the spring and a second end coupled to the arm support segment such that, as the arm support segment is lowered, the pulley moves towards the pivot as the moving axle moves along the track towards the pivot to reduce the offset force applied to the arm support segment, and, as the arm support segment is raised, the pulley moves away from the pivot as the moving axle moves along the track away from the pivot to increase the offset force applied to the arm support segment.

14. A system for supporting an arm of a user, comprising:
a harness configured to be worn on a body of a user;
an arm support comprising a first arm support segment pivotally coupled to the harness about a first vertical axis such that the first arm support segment is rotatable substantially horizontally about the first vertical axis relative to the harness, and a second arm support segment pivotally coupled to the first arm support segment at a hub such that the second arm support segment is rotatable about a second axis generally orthogonal to the first vertical axis; and
one or more compensation elements to apply an offset force to at least partially offset a gravitational force acting on the arm as the user moves and the arm support follows the movement of the user's arm, the one or more compensation elements comprising:
a cam plate fixedly coupled to the hub and including a cam slot;
a moving axle slidably mounted within a chassis slot in a chassis of the second arm support segment, the moving axle slidably disposed within the cam slot of the cam plate such that the moving axle moves along the cam slot and within the chassis slot as the second arm support segment is raised and lowered; and
a spring including a first fixed end and a second end coupled to the moving axle such that the offset force increases as the moving axle moves along the cam slot away from the second axis and decreases as the moving axle moves along the cam slot towards the second axis.

\* \* \* \* \*